(12) United States Patent
Darvish et al.

(10) Patent No.: US 7,460,907 B1
(45) Date of Patent: Dec. 2, 2008

(54) PACING WITH HEMODYNAMIC ENHANCEMENT

(75) Inventors: Nissim Darvish, Haifa (IL); Bella Felsen, Haifa (IL); Itzik Shemer, Haifa (IL); Judith Kornfeld, Haifa (IL)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/720,639

(22) PCT Filed: Jul. 18, 1999

(86) PCT No.: PCT/IL99/00392

§ 371 (c)(1),
(2), (4) Date: May 16, 2001

(87) PCT Pub. No.: WO00/04947

PCT Pub. Date: Feb. 3, 2000

(30) Foreign Application Priority Data

Jul. 20, 1998 (IL) ........................... 125424

(51) Int. Cl.
*A61N 1/362* (2006.01)

(52) U.S. Cl. .......................................... 607/9

(58) Field of Classification Search ............... 607/4–9, 607/11, 13–15, 17, 18, 72, 74
See application file for complete search history.

(56) References Cited

U.S. PATENT DOCUMENTS

| | | | |
|---|---|---|---|
| 3,572,345 A | 3/1971 | Auphan | |
| 3,587,567 A | 6/1971 | Schiff | |
| 3,651,805 A | 3/1972 | Breiling | |
| 3,942,536 A | 3/1976 | Mirowski et al. | |
| 3,952,750 A | 4/1976 | Mirowski et al. | |
| 4,030,509 A | 6/1977 | Hellman et al. | |
| 4,106,494 A | 8/1978 | McEachern | |
| 4,164,216 A | 8/1979 | Person | |
| 4,184,493 A | 1/1980 | Langer et al. | |
| 4,202,340 A | 5/1980 | Langer et al. | |
| 4,223,678 A | 9/1980 | Langer et al. | |

(Continued)

FOREIGN PATENT DOCUMENTS

EP 148687 7/1985

(Continued)

OTHER PUBLICATIONS

J. L. Wessale et al., "Stroke Volume and Three Phase Cardiac Output Rate Relationship with Ventricular Pacing", *PACE* 13, May 1990, pp. 673-680.

(Continued)

*Primary Examiner*—George R Evanisko
(74) *Attorney, Agent, or Firm*—WolfBlock LLP; William H. Dippert

(57) ABSTRACT

Apparatus (170) for heart pacing with hemodynamic improvement, including one or more electrodes (36), which convey electrical signals to respective cardiac muscle segments. Signal generation circuitry (50) applies an extended pacing signal (60, 61), having an overall duration greater than three times a chronaxie time, to the one or more electrodes so as to pace the heart. The signal preferably includes a train of a plurality of biphasic pulses, and has an amplitude at least three times as great as a threshold for pacing the heart, but not sufficient for cardioversion.

78 Claims, 9 Drawing Sheets

U.S. PATENT DOCUMENTS

| | | | |
|---|---|---|---|
| 4,237,895 A | 12/1980 | Johnson | |
| 4,273,114 A | 6/1981 | Barkalow et al. | |
| 4,312,354 A | 1/1982 | Walters | |
| 4,316,472 A | 2/1982 | Mirowski et al. | |
| 4,384,585 A | 5/1983 | Zipes | |
| 4,387,717 A | 6/1983 | Brownlee et al. | |
| 4,403,614 A | 9/1983 | Engle et al. | |
| 4,407,288 A | 10/1983 | Langer et al. | |
| 4,440,172 A | 4/1984 | Langer | |
| 4,506,680 A | 3/1985 | Stokes | |
| 4,543,738 A | 10/1985 | Mower | |
| 4,543,956 A | 10/1985 | Herscovici | |
| 4,554,922 A | 11/1985 | Prystowsky | |
| 4,559,946 A | 12/1985 | Mower | |
| 4,559,947 A | 12/1985 | Renger et al. | |
| 4,566,456 A | 1/1986 | Koning | |
| 4,572,191 A | 2/1986 | Mirowski et al. | |
| 4,628,934 A | 12/1986 | Pohndorf et al. | |
| 4,651,716 A | 3/1987 | Forester | |
| 4,665,609 A | 5/1987 | Henry et al. | |
| 4,674,508 A | 6/1987 | DeCote | |
| 4,679,572 A | 7/1987 | Baker, Jr. | |
| 4,690,155 A | 9/1987 | Hess | |
| 4,726,279 A | 2/1988 | Kepler et al. | |
| 4,726,379 A | 2/1988 | Altman et al. | |
| 4,765,341 A | 8/1988 | Mower et al. | |
| 4,821,724 A * | 4/1989 | Whigham et al. | 607/13 |
| 4,830,006 A | 5/1989 | Haluska et al. | |
| 4,928,688 A | 5/1990 | Mower | |
| 4,971,058 A | 11/1990 | Pless et al. | |
| 4,979,507 A | 12/1990 | Heinz et al. | |
| 4,998,531 A | 3/1991 | Bocchi et al. | |
| 5,003,976 A | 4/1991 | Alt | |
| 5,018,522 A * | 5/1991 | Mehra | 607/10 |
| 5,020,544 A | 6/1991 | Dahl et al. | |
| 5,022,396 A | 6/1991 | Watanabe | |
| 5,044,375 A | 9/1991 | Bach, Jr. et al. | |
| 5,083,564 A | 1/1992 | Scherlag | |
| 5,087,243 A | 2/1992 | Avitall | |
| 5,097,832 A | 3/1992 | Buchanan | |
| 5,111,815 A | 5/1992 | Mower | |
| 5,129,394 A | 7/1992 | Mehra | |
| 5,137,021 A | 8/1992 | Wayne et al. | |
| 5,154,501 A | 10/1992 | Svenson et al. | |
| 5,156,147 A | 10/1992 | Warren et al. | |
| 5,156,149 A | 10/1992 | Hudrlik | |
| 5,161,527 A | 11/1992 | Nappholz | |
| 5,163,428 A | 11/1992 | Pless | |
| 5,172,699 A | 12/1992 | Svenson et al. | |
| 5,184,620 A | 2/1993 | Cudahy et al. | |
| 5,199,428 A | 4/1993 | Obel et al. | |
| 5,205,284 A * | 4/1993 | Freeman | 607/10 |
| 5,213,098 A | 5/1993 | Bennett et al. | |
| 5,236,413 A | 8/1993 | Feiring | |
| 5,281,219 A | 1/1994 | Kallok | |
| 5,282,785 A | 2/1994 | Shapland et al. | |
| 5,284,491 A | 2/1994 | Sutton et al. | |
| 5,286,254 A | 2/1994 | Shapland et al. | |
| 5,305,745 A | 4/1994 | Zacouto | |
| 5,320,642 A | 6/1994 | Scherlag | |
| 5,320,643 A | 6/1994 | Roline et al. | |
| 5,327,887 A | 7/1994 | Nowakowski | |
| 5,346,506 A | 9/1994 | Mower et al. | |
| 5,353,800 A | 10/1994 | Pohndorf | |
| 5,366,486 A | 11/1994 | Zipes et al. | |
| 5,368,040 A | 11/1994 | Carney | |
| 5,370,665 A | 12/1994 | Hudrlik | |
| 5,386,837 A | 2/1995 | Sterzer | |
| 5,387,419 A | 2/1995 | Levy | |
| 5,391,192 A | 2/1995 | Lu | |
| 5,391,199 A | 2/1995 | Ben-Haim | |
| 5,398,683 A | 3/1995 | Edwards | |
| 5,415,629 A | 5/1995 | Henley | |
| 5,417,717 A | 5/1995 | Salo et al. | |
| 5,419,763 A | 5/1995 | Hildebrand | |
| 5,425,363 A | 6/1995 | Wang | |
| 5,431,688 A | 7/1995 | Freeman | |
| 5,443,485 A | 8/1995 | Housworth | |
| 5,443,489 A | 8/1995 | Ben-Haim | |
| 5,447,520 A | 9/1995 | Spano | |
| 5,447,525 A | 9/1995 | Powell et al. | |
| 5,458,568 A | 10/1995 | Racchini et al. | |
| 5,464,020 A | 11/1995 | Lerner | |
| 5,468,254 A | 11/1995 | Hahn | |
| 5,472,453 A | 12/1995 | Alt | |
| 5,476,484 A | 12/1995 | Hedberg | |
| 5,476,485 A | 12/1995 | Weinberg et al. | |
| 5,476,497 A | 12/1995 | Mower | |
| 5,482,052 A | 1/1996 | Lerner | |
| 5,499,971 A | 3/1996 | Shapland et al. | |
| 5,501,662 A | 3/1996 | Hofman | |
| 5,514,162 A | 5/1996 | Bornzin et al. | |
| 5,520,642 A | 5/1996 | Bigagli et al. | |
| 5,531,764 A | 7/1996 | Adams et al. | |
| 5,540,722 A | 7/1996 | Clare | |
| 5,549,646 A | 8/1996 | Katz et al. | |
| 5,556,421 A | 9/1996 | Prutchi | |
| 5,568,809 A | 10/1996 | Ben-Haim | |
| 5,571,143 A | 11/1996 | Hoegnelid et al. | |
| 5,584,803 A | 12/1996 | Stevens | |
| 5,584,868 A | 12/1996 | Salo et al. | |
| 5,587,200 A | 12/1996 | Lorenz | |
| 5,601,609 A | 2/1997 | Duncan | |
| 5,601,611 A | 2/1997 | Fayram et al. | |
| 5,620,468 A | 4/1997 | Mongeon et al. | |
| 5,626,622 A | 5/1997 | Cooper | |
| 5,634,899 A | 6/1997 | Shapland et al. | |
| 5,649,966 A | 7/1997 | Noren et al. | |
| 5,651,378 A | 7/1997 | Matheny | |
| 5,662,687 A | 9/1997 | Hedberg et al. | |
| 5,674,251 A | 10/1997 | Combs et al. | |
| 5,674,259 A | 10/1997 | Gray | |
| 5,683,429 A * | 11/1997 | Mehra | 607/14 |
| 5,683,431 A | 11/1997 | Wang | |
| 5,687,734 A | 11/1997 | Dempsey et al. | |
| 5,697,953 A | 12/1997 | Kroll et al. | |
| 5,713,935 A | 2/1998 | Prutchi et al. | |
| 5,720,768 A | 2/1998 | Verboven-Nelissen | |
| 5,735,876 A | 4/1998 | Kroll et al. | |
| 5,738,096 A | 4/1998 | Ben Haim | |
| 5,738,105 A | 4/1998 | Kroll | |
| 5,749,906 A | 5/1998 | Kieval et al. | |
| 5,755,740 A | 5/1998 | Nappholz | |
| 5,782,876 A | 7/1998 | Flammang | |
| 5,782,881 A | 7/1998 | Lu et al. | |
| 5,792,198 A | 8/1998 | Nappholz | |
| 5,792,208 A | 8/1998 | Gray | |
| 5,797,967 A | 8/1998 | KenKnight | |
| 5,800,464 A | 9/1998 | Kieval | |
| 5,807,234 A | 9/1998 | Bui et al. | |
| 5,807,306 A | 9/1998 | Shapland et al. | |
| 5,814,079 A | 9/1998 | Kieval | |
| 5,865,787 A | 2/1999 | Shapland et al. | |
| 5,871,506 A | 2/1999 | Mower | |
| 5,906,607 A | 5/1999 | Taylor et al. | |
| 5,906,633 A * | 5/1999 | Mouchawar et al. | 607/5 |
| 5,913,876 A | 6/1999 | Taylor et al. | |
| 5,927,284 A | 7/1999 | Borst et al. | |
| 5,978,703 A * | 11/1999 | Kroll et al. | 607/5 |
| 6,032,074 A | 2/2000 | Collins | |
| 6,032,672 A | 3/2000 | Taylor | |
| 6,041,252 A | 3/2000 | Walker et al. | |
| 6,071,305 A | 6/2000 | Brown et al. | |
| 6,086,582 A | 7/2000 | Altman et al. | |

| | | | |
|---|---|---|---|
| 6,136,019 A | 10/2000 | Mower | |
| 6,141,586 A * | 10/2000 | Mower | 607/9 |
| 6,151,586 A | 11/2000 | Brown | |
| 6,178,351 B1 | 1/2001 | Mower | |
| 6,295,470 B1 | 9/2001 | Mower | |
| 6,311,089 B1 * | 10/2001 | Mann et al. | 607/30 |
| 6,337,995 B1 | 1/2002 | Mower | |
| 6,341,235 B1 | 1/2002 | Mower | |
| 6,343,232 B1 | 1/2002 | Mower | |
| 6,411,847 B1 | 6/2002 | Mower | |
| RE38,119 E | 5/2003 | Mower | |

FOREIGN PATENT DOCUMENTS

| | | | |
|---|---|---|---|
| EP | 0314078 B1 | | 5/1989 |
| EP | 727 241 | | 8/1996 |
| JP | 62275471 | | 11/1987 |
| JP | 04117967 A2 | | 4/1992 |
| JP | 4365493 | | 12/1992 |
| JP | 7126600 | | 5/1995 |
| WO | WO 92/00716 | | 1/1992 |
| WO | WO 95/08316 | | 9/1995 |
| WO | WO 96/16696 | | 6/1996 |
| WO | WO 9810831 | | 9/1996 |
| WO | WO 97/25101 | | 1/1997 |
| WO | WO 97/25098 | * | 7/1997 |
| WO | WO 98/10828 | | 3/1998 |
| WO | WO 98/10830 | | 3/1998 |
| WO | WO 98/10831 | | 3/1998 |
| WO | WO 98/10832 | | 3/1998 |
| WO | WO 98/19719 | | 4/1998 |
| WO | WO 00/04947 | | 2/2000 |

OTHER PUBLICATIONS

A. Wirtzfeld et al., "Physiological Pacing: Present Status and Future Developments", *PACE* 10 Jan.-Feb. 1987, Part 1, pp. 41-57.

U. Talit et al., "The Effect of External Cardiac Pacing on Stroke Volume", *PACE* 13, May 1990, pp. 598-602.

John G. Webster, ed., *Design of Cardiac Pacemakers*, IEEE Press, Piscataway, New Jersey, 1995.

E. S. Fain et al., "Improved Internal Defibrillation Efficacy with a Biphasic Waveform", *American Heart Journal* 117(2), Feb. 1989, pp. 358-364.

Fromer et al., "Ultrarapid Subthreshold Stimulation for Termination of Atrioventricular Node Reentrant Tachycardia", *Journal of the American College of Cardiology* 20 (Oct. 1992), pp. 879-883.

Knisley et al., "Prolongation and Shortening of Action Potentials by Electrical Shocks in Frog Ventricular Muscle", *American Journal of Physiology* 6 (*Heart Circ. Physiol.* 35, 1994) pp. H2348-H2358.

Thakor et al., "Effect of Varying Pacing Waveform Shapes on Propagation and Hemodynamics in the Rabbit Heart", *The American Journal of Cardiology* 79(6A), pp. 36-43. 1997.

M. R. Franz, "Method and Theory of Monophasic Action Potential Recording", *Prog. Cardiovasc Dis* 33(6), May-Jun. 1991, pp. 347-368.

M.R.Franz, "Bridging the Gap between Basic and Clinical Electrophysiology: What Can Be Learned from Monophasic Action Potential Recordings?", *J. Cardiovasc Electrophysiol* 5(8), Aug. 1994, pp. 699-710.

K. Bargheer et al., "Prolongation of Monophasic Action Potential Duration and the Refractory Period in the Human Heart by Tedisamil, a New Potassium-Blocking Agent", *J. Eur Heart* 15(10), Oct. 1994, pp. 1409-1414.

M.R. Franz, "Progress in Cardiovascular Diseases: Monophasic Action Potential Symposium, I. Intoduction", *Prog. Cardiovasc Dis* 33(6), May-Jun. 1991, pp. 345-346.

E. R. McVeigh et al., "Noninvasive Measurement of Transmural Gradients in Myocardial Strain with MR Imaging", *Radiology* 180(3), Sep. 1991, pp. 677, 679-684.

D. M. Bers, *Excitation-Contraction Coupling and Cardiac Contractile Force*. 1991.

D. Zipes et al., *Cardiac Electrophysiology from Cell to Bedside*, 1990, W. B. Saunders Co., Philadelphia. 1990.

M. E. Josephson, *Clinical Cardiac Electrophysiology: Techniques and Interpretations*, 2nd Edition, Lea & Febiger, Philadelphia. 1991.

H. Antoni et al., "Polarization Effects of Sinusoidal 50 Hz Alternating Current on Membrane Potential of Mammalian Cardiac Fibres", 1970.

Josephson, M.E., Clinical Cardiac Electrophysiology: Techniques and Interpretations, 2nd Edition, Lea & Febiger, Philadelphia, 1991, Chapters 3 and 15.

Morse, et al., A Guide to Cardiac Pacemakers, Defibrillators and Related Products, Droege Computing Services, Durham, NC, pp. 2-1 to 2-8.

Merck Manual, The, Section 3, the 16th Edition of the Merck Manual, Published 1992, pp. 471-473.

Saksena et al., Prevention of Recurent Atrial Fibrillation With Chronic Dual-Site Right Atrial Pacing', JACC, vol. 28, No. 3, Sep. 1996, pp. 687-694.

Webster, John G., ed., Design of Cardiac Pacemakers, IEEE Press, Piscataway, New Jersey, 1995, Chapters 5, 9, and 13-16.

Zipes, D., et al., Cardiac Electrophysiology from Cell to Bedside, 1990 W.B. Saunders Co., Philadelphia, Chapters 87, 99-102, and 104.

"The Latest Tetralogy of Fallot Discussion with Graphical Support including Video of Echocardiography and Catherization" Pediatric Electrophysiologypicu Book ("An Online Resource for Pediatric Critical Care"), 1998.

Antman, E.M. et al. "Treatment of 150 Cases of Life-Threatening Digitalis Intoxication with Digoxin-Specific Fab Antibody Fragments;" Jun. 1990 Circulation; vol. 81: No. 6: pp 1744-1752.

Antoni, H. et al. "Polarization Effects of Sinusoidal 50-Cycle Alternating Current on Membrane Potential of Mammalian Cardiac Fibers", Pfluegers Arch. 314, pp. 274-291 (1970).

Bach, S.M., Tach Arrhythmia Detection, Implantable Cardioverter Defibrilator Therapy: The Engineering-Clinical Interface, Chapter 15, pp. 303-323, Eds, Mark W. Kroll and Michael H. Lehmann, Kluwer Academic Publishers, USA, 1997.

Bakker, P.F., et al., "Beneficial Effects of Biventricular Pacing of Congestive Heart Failure", PACE, vol. 17, Apr. 1994, Part 11, one page.

Bakker, P.F., et al., "Biventricular Pacing Improves Functional Capacity in Patients with End-Stage Congestive Heart Failure" PACE, vol. 17, Apr. 1995, Part 11, one page.

Bargheer K. et al., "Prologation of Monophasic Action Potential Duration and the Refractory Period in the Human Heart by Tedisamil, a New Potassium-Blocking Agent", J. Eur Heart 15 (10), Oct. 1994, pp. 1409-1414.

Borst, et al. "Coronary Artery Bypass Grafting Without Cardiopulomonary Bypass and Without Interuption of Native Coronary Flow Using a Novel Anastomosis site restraining device ('Octupus')", Journal of the American College of Cardiology, 27 (6), May 1996.

Cano, N.J. et al. "Dose-Dependent Reversal of Digoxin-Inhibited Activity of an In-Vitro NA+K+ATPase Model by Digoxin-Specific Antibody;" May 1996; pp. 107-1011; Toxicology Letters; vol. 85; No. 2.

Cazeau S. et al., "Multisite Pacing for End-Stage Heart Failure: Early Experience", Pacing and Clinical Electrophysiology vol. 19, Nov. 1996, Part 11, pp. 1748-1757.

Cooper, W., "Postextrasystolic Potentiation: Do We Really Know What It Means and How to Use It?" Circulation, vol. 88, No. 6, Dec. 1993, pp. 2962-2971.

Dillon, SM., "Optical Recordings in the Rabbit Heart Show that Defibrillation Strength Shocks Prolong the Duration of Depolarization and the Refractory Period" in Circ Res., 69 (3), Sep. 1991, pp. 842-856.

Dillon, SM., abstract of "Synchronized Repolarization After Defibrillation Shocks. A Possible Component of the Defibrillation Process Demonstration By Optical Recordings in Rabbit Heart", Circulation, May 1992, vol. 85, No. 5, pp. 1865-1878.

Fain, E.S., et al. "Improved Internal Defibrillation Efficacy with a Biphasic Waveform", American Heart Journal 117 (2), Feb. 1989, pp. 358-364.

Fleg, J.L. et al., "Impact of Age on the Cardiovasvular Response to Dynamic Upright Exercise in Healthy Men and Women", J. Appl. Physiol., vol. 78, 1995, p. 890.

Foster, A.H, et al., "Acute Hemodynamic Effects of Atrio-Biventricular Pacing in Humans", 1995, The Society of Thoracic Surgeons vol. 59, pp. 294-299.

Franz, M.R., "Bridging the Gap Between Basic and Clinical Electrophysiology: What Can be Learned from Monophasic Action Potential Recordings?", J. Cardiovasc Electrophysiol 5(8), Aug. 1994, pp. 699-710.

Franz, M.R., "Method and Theory of Monophasic Action Potential Recording", Prog. Cardiovasc Dis 33 (6), May-Jun. 1991, pp. 347-368.

Franz, M.R., "Progress in Cardiovascular Disease: Monophasic Action Potential Symposium, I. Introduction", Prog. Cardiovasc Dis 33 (6), May-Jun. 1991 pp. 345-346.

Fu. P and B.J. Bardakjian, "System Identification of Electrically Coupled Smooth Muscle Cells: The Passive Electrically Coupled Smooth Muscle Cells: The Passive Electrical Properties", published in IEEE Transactions on Biomedical Engineering, 38(11), pp. 1130-1140, 1991.

Ham, Frederic M and Han, Soowhan, "Classification of Cardiac Arrhythmias Using Fuzzy Artmap"; IEEE Transactions on Biomedical Engineering, vol. 43, No. 4, Apr. 1996.

Hoffman, B.F. et al., "Effects of Postextrasystolic Potentiation on Normal & Failing Hearts", Bulletin of New York Academy of Medicine, 41 in 1965, pp. 498-534.

King, A. et al., The Inotropic Action of Paired Pulse Stimulation in the Normal and Failing Heart: An Experimental Study', Cardiovascular Research, vol. 2, Apr. 1968, pp. 122-129.

Knisley et al., "Prolgongation and Shortening of Action Potentials by Electrical Shocks in Frog Ventricular Muscle", American Journal of Physiology 6 (Heart Circ. Physiol. 35, 1994) pp. H2348-H2358.

Koller, et al., "Relation Between Repolarization and Refractoriness During Programmed Electrical Stimulation in the Human Right Ventricle", Circulation 91(9), 2378-2384, 1995.

Langberg, Jonathan J. et al., "Identification of Ventricular Tachycardia with Use of the Morphology of the Endocardial Electrogram", Circulation, vol. 77, No. 6, Jun. 1988.

McVeigh, E.R et al., "Noninvasive Measurement of Transmural Gradients in Myocardial Strain with MR Imaging"; Radiology 180 (3), Sep. 1991, pp. 677, 679-684.

Mercando, A.D., et al., "Automated Detection of Tachardias by Antitachicardia Devices", Chapter 100, pp. 943-948, in Cardiac Electrophysiology from Cell to Bedside, Eds. Douglas P. Zipes and Jose Jalife, publishers W.B. Saunders Company (1990).

Moran, R.J. et al; "Digoxin-Specific Fab Fragments Impair Renal Function in the Rat:" 1994; pp. 854-856: Journal of Pharmacy and Pharmacology; vol. 46: No. 10.

Paul, V.E., et al. "Automatic Recognition of Ventricular Arrythmias Using Temporal Electrogram Anaylsis" Pace, vol. 14, pp. 1265-1273, (1991).

Qiuzhen Xue et al., "Neural-Network-Based Adaptive Matched Filtering for QRS Detection", IEEE Transactions on Biomedical Engineering, vol. 39, No. 4. Apr. 1992.

Shumaik, G.M. et al, "Oleander Poisoning; Treatment with Digoxin-Specific Fab Antibody Fragments;" Jul. 1988; pp. 732-735; Annals of Emergency Medicine; vol. 17; No. 7.

Sweeny RJ, et al., abstract of "Countershock Strength-Duration Relationship for Myocardial Refractory Period Extension", Acad Emerg. Med., Jan. 1995, vol. 2, No. 1, pp. 57-62.

Sweeny RJ, et al., abstract of "Refractory Interval After Transcardiac Shocks During Ventricular Fibrillation", Circulation, Dec. 1996, vol. 94, No. 11, pp. 2947-2952.

Sweeny RJ, et al., abstract of "Ventricular Refractory Period Extension Caused by Defibrillation Shocks", Circulation, Sep. 1990, vol. 82, No. 3, pp. 965-972.

Talit, U. et al., "The Effect of External Cardiac Pacing on Stroke Volume", Pace 13, May 1990, pp. 598-560.

Tsong, T.Y., "Electroportion of Cell Membranes" Aug. 1991; pp. 297-306; Biophysical Journal; vol. 60.

Verrier, et al., "Electrophysiologic Basis for T Wave Alternans as an Indeox of Vulnerability to Ventricular Fabrillation" Journal of Cardiovascular Electrophysiology, vol. 5, pp. 445-461, 1994.

Wessale, J.L. et al., "Stroke Volume and Three Phase Cardiac Output Rate Relationship with Ventricular Pacing" Pace 13, May 1990, pp. 673-680.

Wirtzfeld, A. et al., "Physiological Pacing: Present Status and Future Developments", Pace 10 Jan.-Feb. 1987, Part I, pp. 41-57.

Guidant Product Catalogue, 2001, 2 pages.

Brumwell D.A. et al. "The Amplifier: Sensing the Depolarization", Implantable Cardioverter Defibrillator Therapy: The Engineering-Clinical Interface, Chapt. 14, pp. 275-302, Eds. Kroll and Lehmann, Kluwer Academic Publishers, USA 1997.

Gill RJ, et al., abstract of "Refractory Period Extension During Ventricular Pacing at Fibrillatory Pacing Rates" Pacing Clin. Electrophysiol, Mar. 1997, vol. 20, No. 3, pp. 647-653.

Hardage, M.L. and Sweeney, M.B., "Anti-Tachycardia Pacing and Cardioversion", Implantable Cardiovertre Defibrillator Therapy: The Engineering-Clinical Interface, Chapt. 6, pp. 325-342, Eds. Mark W. Kroll and Michael H. Lehmann, Kluwar Academic Publishers U.S.A 1997.

Matheny R.G. and C.J. Shaar, "Vagus Nerve Stimulation as a Method to Temporarily Slow or Arrest the Heart" Annals of Thoracic Surgery. 63 (6) Supplement, pp. S28-S29, Jun. 1997.

Supino, C.G., "The System", Implantable Cardioverter Defibrillator Therapy: The Engineering-Clinical Interface, Chapt. 8, pp. 163-172, Eds. Mark W. Kroll and Michael H. Lehmann, Kluwer Academic Publishers, USA 1997.

* cited by examiner

PACING WITH HEMODYNAMIC ENHANCEMENT

FIELD OF THE INVENTION

The present invention relates generally to cardiac therapeutic devices, and specifically to cardiac pacemakers.

BACKGROUND OF THE INVENTION

In certain heart diseases, either congenital or acquired, natural pacing is replaced or assisted by artificial pacing induced by a pacemaker, which is generally implanted in the patient's chest. Pacemakers known in the art provide artificial excitatory pulses to the heart tissue to control the heart rhythm. Early pacemakers were asynchronous pulse generators that operated at a fixed invariant rate. Later, demand type pacemakers were developed, in which stimulation pulses are produced only when a naturally-occurring heartbeat is not detected within some maximum type period.

Cardiac pacemakers are required to deliver a stimulus pulse of sufficient magnitude and duration to cause an action potential to propagate from the point of excitation, leading to heart muscle contraction. Thus, the primary function of a pacemaker is to regulate heart rhythm rather than the contractility of the muscle. Furthermore, it is known in the art that the use of a pacemaker generally results in decreased contractility of the cardiac muscle and, consequently, a decreased cardiac output (CO) for a given heart rate.

The hemodynamic effect of different types of pacemakers has long been researched. For example, Wessale et al., in an article entitled "Stroke Volume and Three Phase Cardiac Output Rate Relationship with Ventricular Pacing," *Pacing Clin Electophysiol* 13 (May, 1990), pp. 673-680, describe a three-phase relationship between pacing rate and cardiac output. At a low pacing rate CO increases with increasing rate. There is an intermediate range of rates in which CO stays steady, and above which a further rate increase will cause a decrease in CO. This, of course, causes a major problem for the patient, since a demand for a higher pacing rate typically stems from a demand for an increase in tissue oxygen supply. Research and clinical experience show that with various types of pacemakers, some cardiac output augmentation may take place initially, but is not maintained on a long-term basis and may even deteriorate compared to the situation before beginning pacing. (See, for example, Wirtzfeld et al., "Physiological Pacing: Present Status and Future Developments," *Pacing Clin Electrophysiol* 10 (January, 1987), pp. 41-47.

Talit et al., in "The Effect of External Cardiac Pacing on Stroke Volume," *Pacing Clin Electophysiol* 13 (May, 1990), pp. 598-602, evaluated the hemodynamic effects of external cardiac pacing on ten subjects and found a decrease of 23% in stroke volume and 14% decrease in cardiac output when compared to the values of these parameters that were obtained prior to pacing.

It is a principle of pacing that the optimal pacing mode is that which gives optimal hemodynamics, thus making the patient the most comfortable. This principle has guided researchers to attempt to regulate the mechanical performance of the heart by synchronization of the contraction of the heart chambers using sequential A/V or multisite pacing. Attempts have also been made to provide pacemakers with improved physiological sensing capabilities, for use in giving feedback to the pacemaker.

FIG. 1A is a schematic diagram illustrating elements of a pacemaker pulse generator 20 for pacing a heart 22, as is known in the art. Such pacemakers are described, for example, in *Design of Cardiac Pacemakers*, John G. Webster, ed. (IEEE Press, Piscataway, N.J., 1995), which is incorporated herein by reference. Pacemaker 20 comprises a battery 24 or other power source, which charges a tank capacitor 28 via a charge pump 26 (or voltage multiplier). To apply a pacing pulse to heart 22, a switch 30 is closed, transferring stored charge from capacitor 28 via a DC-blocking capacitor 34 to electrodes 36. Switch 30 is then opened, and a discharge switch 32 is preferably closed in order to remove charge buildup on capacitor 28.

FIG. 1B is a timing diagram illustrating a typical pacing signal 38 generated by pacemaker 20 across electrodes 36. Switch 30 is closed for a very short period, typically between 0.1 and 1.5 ms in order to produce a sharp, narrow, cathodic (negative voltage) pacing pulse 40 with a total discharge of 0.1-50 µC. The amplitude and duration of the pulse are programmable in order to adjust the stimulus that is applied to the heart. Typically, for safety and reliability of pacing, the amplitude of the pulse is set empirically to roughly twice the rheobase, which is the minimum electrical current that will cause the myocardial cell membranes to depolarize. The pacing pulse duration is set to up to twice the chronaxie time, which is the pulse duration that will cause depolarization at twice the rheobase current. A longer duration or higher amplitude has been considered undesirable, because it would tend to discharge battery 24 prematurely without any improvement in the pacemaker performance or in the physiological performance of the heart or the safety of the pacing. In fact, substantial research and product development efforts in the pacing field have been dedicated to finding pacing methods and waveforms that reduce the amount of energy that must be applied to the heart, in order to prolong battery and circuit lifetime.

After pacing switch 30 is opened, discharge switch 32 is closed, typically for about 20 ms, causing an anodic (positive voltage) discharge phase 42 to appear across electrodes 36. The specific duration and amplitude of this phase of the pacing waveform are not significant from the point of view of pacing, since it is intended only to remove residual charge and does not provide any stimulation to the heart.

A number of authors have suggested varying the shape and/or duration of the pacing pulse in order to obtain improved pacing effects or to reduce the pulse amplitude or charge flux needed to provide a desired level of stimulation. Among other techniques, biphasic pulses (including both cathodic and anodic portions) or bursts of pulses have been used for defibrillation and antitachycardic pacing.

For example, U.S. Pat. No. 5,531,764 to Adams et al. describes an implantable defibrillator having programmable shock waveforms of different shapes and magnitudes in different combinations and sequences.

Fain et al., in their work "Improved Internal Defibrillation Efficacy with a Biphasic Waveform," in the *American Heart Journal* 117 (February, 1989), pp. 358-64, show that a biphasic truncated exponential shock waveform significantly reduces the initial voltage and energy requirements for effective defibrillation.

Fromer et al., in an article entitled "Ultrarapid Subthreshold Stimulation for Termination of Atrioventricular Node Reentrant Tachycardia," in Journal of the American College of Cardiology 20 (October, 1992), pp. 879-83, describe the application of a train of stimuli to intracardiac electrodes in order to terminate tachycardic episodes without the need for cardioversion. The train ranged from 4 to 16 pulses, each 2 ms long. The pulse train was thus meant, under certain circumstances, to take the place of or precede more drastic defibrillative measures, and not to pace the heart.

Similarly, Hedberg, et al., in U.S. Pat. No. 5,622,687, describe an implantable defibrillator which applies a train of low-energy defibrillation pulses in order to defibrillate the heart with a lower total energy flux than would ordinarily be required using conventional defibrillation pulses. The train includes between 2 and 10 pulses, preferably about 10 ms apart. The width of the pulses is not specified. The pulses may be either monophasic or biphasic. In any case, the clinical and technical considerations in generating signals of the type employed by a defibrillator are entirely different from those involved in pacing the heart.

Kinsley, et al., in an article entitled "Prolongation and Shortening of Action Potentials by Electrical Shocks in Frog Ventricular Muscle," in the *American Journal of Physiology* 6 (*Heart Circ. Physiol.* 35, 1994), pp. H2348-H2358, describe measurements of contraction length and intracellular action potential following application of shocks to heart tissue. By varying the strength of the shocks, the contraction strength of the tissue could be increased, and the action potentials lengthened or shortened. The authors propose that such techniques could be used in defibrillation, but make no suggestion with regard to pacing the heart.

U.S. Pat. No. 4,312,354, to Walters, describes a pacemaker with a circuit for pulse width modulation of the stimulus pulses applied to the heart. The purpose of the modulation is not to directly affect the pacing itself, but rather to afford a means for indicating to an external telemetry unit a control state of the pacemaker.

Thakor, et al., in an article entitled "Effect of Varying Pacing Waveform Shapes on Propagation and Hemodynamics in the Rabbit Heart," in *The American Journal of Cardiology* 79 (Mar. 20, 1997), pp. 36-43, describe experiments using biphasic pacing pulses to increase the speed of electrical conduction in heart muscle fibers. Both monophasic and biphasic pulses of 2 to 8 ms total duration were applied to isolated muscle fibers using unipolar electrodes. The biphasic pulses consisted of a single cathodic pulse immediately followed by a single anodic pulse, or vice versa. The article reports that propagation of the resulting electrical potentials along the fibers was significantly faster for the biphasic stimulation. It was observed that pacing with an anodic/cathodic biphasic pulse resulted in faster electrical conduction, and led to an earlier development of pressure in the muscle fiber and a shorter duration of the pressure waveform than did monophasic pulses. The authors suggest that the biphasic pulse could be associated with the ability to augment muscular contraction.

PCT patent application PCT/IL97/00012, published as WO 97/25098, to Ben-Haim et al., which is incorporated herein by reference, describes methods for modifying the force of contraction of at least a portion of a heart chamber by applying a non-excitatory electric field to the heart at a delay after electrical activation of the portion. The non-excitatory field is such as does not induce activation potentials in cardiac muscle cells, but rather modifies the cells' response to the activation. The non-excitatory field may be applied in combination with a pacemaker or defibrillator, which applies an excitatory signal (i.e., pacing or defibrillation pulses) to the heart muscle.

SUMMARY OF THE INVENTION

It is an object of some aspects of the present invention to provide methods and devices for pacing the heart with enhanced contractility of the heart muscle.

It is another object of some aspects of the present invention to provide methods and devices for pacing the heart with modification of pulsatile blood flow dynamics.

It is yet another object of some aspects of the present invention to provide methods and devices for pacing the heart with modulation of action potentials in the myocardium.

It is a further object of some aspects of the present invention to provide methods and devices for pacing the heart with increased cardiac output and/or modification of other cardiac performance parameters such as peak-systolic and end-diastolic pressure, afterload and blood perfusion profile.

In some aspects of the present invention, the enhancement of contractility or increased cardiac output may be alternately activated and de-activated while pacing pulses are applied to the heart.

In preferred embodiments of the present invention, an improved cardiac pacemaker applies an extended pacing signal to the heart, the signal comprising a pacing pulse or a periodic waveform, preferably a train of pulses, having an overall duration substantially longer than a pulse duration required for pacing the heart. Preferably, the overall duration is at least three times the chronaxie time. Further preferably, the overall duration is greater than 8 ms, more preferably, greater than 10 ms, and most preferably, greater than 20 ms. The pulse shape and duration are controlled, however, as described hereinbelow, so as to reduce the risk of arrhythmia that could arise from the long duration of the extended waveform.

Preferably, the electrical current applied in each pulse is substantially greater than twice the threshold required for pacing, and more preferably, greater than three times the threshold, although still substantially less than a level that would be required for cardioversion or defibrillation.

In those preferred embodiments of the present invention wherein the extended pacing signal comprises a periodic waveform, the waveform preferably has a period of at least 2 ms (i.e. repetition frequency of 500 $s^{-1}$), more preferably at least 10 ms, and most preferably at least 20 ms. The extended pacing waveform preferably comprises a pulse train, which is preferably superimposed on a DC offset. Each of the pulses in the train preferably has a duration of at least 1 ms. In some preferred embodiments, the period of the waveform varies over the duration of the signal, preferably increasing towards the end of the signal. Such an increase is believed to be effective in reducing the likelihood of inducing arrhythmias due to the extended overall duration of the signal.

The inventors have found that application of extended pacing signals in accordance with the principles of the present invention engenders a modulation of the action potential, leading to improvement of one or more cardiac performance parameters, particularly in connection with pulsatile blood flow from the heart. Such improvements may include enhanced contraction force of the heart muscle, increased cardiac output (i.e., increased stroke volume), decreased end-diastolic pressure, increased peak-systolic pressure, improved rate of pressure increase (dp/dt), increased afterload, improved cardiac efficacy and flow dynamics profile and improved cardiac index by comparison with pacing waveforms known in the art.

The present invention thus addresses the issue of the hemodynamic effect of the pacemaker in a novel manner. The stimulating signals it applies to the heart not only control the heart rate but also control the heart's contractility and therefore improve the hemodynamics based on a mechanism that has not been used in the art of pacing before and stands in contrast to the negative hemodynamic effects of pacemakers known in the art. Due to the major improvement in hemodynamic function consequent to the use of the present invention, it may benefit not only patients requiring pacemakers for rate control, but also patients who suffer from deteriorating functioning of the heart not necessarily related to the heart rhythm, such as patients who suffer from congestive heart failure (CHF). The extended pacing signals are preferably applied by a pacemaker, but may also be applied by a defibrillator device having a pacemaker backup.

It is believed that the enhancement of contractility in response to the extended pacing signals is due to a mechanism occurring at the individual myocyte level, probably a modification of the action potential due to an increased availability of calcium in heart cell membranes resulting from the pulses. In any case, the operation of the present invention is supported by experimental observation, on both individual muscle fibers and on complete, isolated hearts, as well as in vivo in large animal models, and is not dependent on any particular hypothesis.

It is further noted that the enhancement of cardiac function obtained by application of extended pacing signals in accordance with the principles of the present invention cannot be attributed to any mechanism disclosed in the prior art, such as those described in the above-mentioned article by Thakor et al. Thakor reported a slight improvement in dp/dt in an isolated heart muscle fiber, based on a mechanism of increased propagation speed, while applying pacing pulses and waveforms of substantially shorter duration and lower energy than in the present invention. By applying novel extended pacing signals, however, the present inventors, h, have demonstrated enhancement and control of the heart's pulsatile flow, as well as modulation of action potentials in the heart muscle, which were not observed by Thakor (or reported in the context of pacing by any other prior investigators) and would not have been possible under the experimental conditions described by Thakor.

Applying long-duration signals to the heart muscle may increase the risk of cardiac arrhythmia if some part of the signals extends beyond the absolute refractory period. Under these conditions, any rapid change in voltage applied to the heart can cause an additional, undesired excitation, which can be dangerous or even fatal to the patient, since it may lead to induction of ventricular tachycardia or fibrillation. Therefore, in some preferred embodiments of the present invention, the extended pacing signal has a slowly decaying trailing edge or waveform envelope, rather than terminating sharply as is known in the art. In some of these preferred embodiments, the trailing edge or envelope decays generally linearly or exponentially. In other preferred embodiments of the present invention, wherein the signal comprises a periodic waveform, the period increases over the duration of the signal, thus, when the signal comprises a pulse train, a later pulse or pulses in the train are longer than an earlier pulse or pulses.

Additionally or alternatively, when extended pacing signals are applied at multiple sites in the heart, as described further hereinbelow, the signals are preferably mutually timed responsive to the respective refractory periods at the sites so as reduce or eliminate the possibility of undesired (and possibly fatal) additional excitations. In other words, at each of the sites, the signal is terminated before the end of the respective refractory period. Properly synchronized multisite application of the signals both increases the safety of the pacemaker and aids in synchronizing the contraction of two or more of the heart chambers.

In some preferred embodiments of the present invention, the pacemaker receives signals indicative of physiological parameters related to cardiac function, such as heart rate, cardiac output. LVP, ECG, or dp/dt of the left or right ventricle, and controls the application of the extended pacing signals responsive to the received cardiac function signals. In one such preferred embodiment, the pacemaker applies the extended pacing signals when the parameters are outside a predetermined range of desired values, for example, when the cardiac output is low. Alternatively or additionally, the pacemaker receives electrophysiological signals indicative of the propagation of action potentials in the heart. The signals are analyzed to detect the possible presence of abnormal activation in the heart. When the possibility of abnormal activation is detected, the pacemaker preferably modifies the extended pacing signals, for example, by reducing their duration and/or amplitude and/or the number of pulses in the train.

In one of these preferred embodiments, the electrophysiological signals comprise Monophasic Action Potentials (MAP), as are known in the art, which are preferably used to determine the duration of the refractory period and/or to detect abnormal local electrical activity at or adjacent to a pacing site in the heart. Principles and techniques of MAP measurement are described, for example, by M. R. Franz in "Method and Theory of Monophasic Action Potential Recording," *Prog Cardiovasc Dis* 33(6) (May-June, 1991), pp. 347-368, and in "Bridging the Gap between Basic and Clinical Electrophysiology: What Can Be Learned from Monophasic Action Potential Recordings?" in *Cardiovasc Electrophysiol* 5(8) (August, 1994), pp. 699-710, which are incorporated herein by reference. The pacemaker preferably controls the extended pacing signal so that the pacing signal duration does not exceed that of the refractory period.

In another preferred embodiment, the electrophysiological signals are captured using close bipolar sensing, wherein local electrical activity of the heart tissue is measured using two small electrodes a short distance apart. A differential signal measured between the two electrodes reflects propagation of the action potentials in a small area, having dimensions on the order of the distance between the electrodes. The differential signal is thus used to determine the time of onset and the duration of the local action potential at the location of the electrode and to accurately observe changes in the action potential due to application of the extended pacing signals. As described above, the pacemaker preferably controls the extended pacing signal so that the pacing signal duration does not exceed that of the refractory period and/or to discontinue the extended pacing signals if abnormal local electrical activity is observed to result from the pacing.

Further alternatively or additionally, cardiac electrophysiological activity is mapped prior to application of the pacing electrodes. The map thus generated is used in determining where the pacing electrode or electrodes should be positioned and/or in programming and controlling the extended pacing waveform.

In some preferred embodiments of the present invention, the extended pacing signal comprises a train of biphasic pulses. The inventors have observed that application of a train of two or more biphasic pulses, each pulse preferably having a duration of at least 5 ms, and more preferably at least 8-10 ms, substantially enhances the effect of increased contractility and cardiac output.

In some preferred embodiments of the present invention, the extended pacing signals are applied using one or more intracardiac electrodes, applied to the endocardium, and operating in either a unipolar or, more preferably, a bipolar configuration. The electrodes are preferably made of highly conductive material with a large effective surface area. When multiple electrodes are used, different ones of the electrodes may have different surface areas or different shapes, for example, elongated or patch shapes.

In some of these preferred embodiments, pacing signals are applied using multiple electrodes at different, respective sites in the heart, in one or more of the heart's chambers. In such embodiments, the signals are preferably applied to the different sites in sequence, timed and programmed so as to maximize a desired enhancement of cardiac function. In one such preferred embodiment, one of the multiple electrodes, which is preferably positioned in one of the atria of the heart, applies conventional pacing pulses, while another of the electrodes, preferably in one of the ventricles, applies the extended pacing signals. Other combinations and configurations are also possible and are within the scope of the present invention; and the application of the extended pacing signals can be incorporated into substantially any mode of pacing known in the art, including (but not limited to) VOO, VVI, OVO, VVT, VVIR, VDT, AOO. AAIR, ADI, VDD, DDD and DDTv pacing. Preferably, the electrodes are positioned and the pacing signals are programmed and controlled responsive to a map of cardiac electrical activity, as described hereinabove.

In other preferred embodiments of the present invention, the extended pacing pulses are applied using epicardial, transmyocardial or transvenous electrodes or a combination of such electrodes.

In some preferred embodiments of the present invention, the extended pacing signals are applied only when hemodynamic enhancement is desired, as described hereinabove, so as to conserve energy and extend the lifetime of a battery that powers the pacemakers. Preferably, when the extended pacing signal is not applied, the pacemaker applies conventional pacing pulses, as are known in the art, to pace the heart, or applies no pulses at all. Further preferably, both the extended pacing waveforms and the conventional pacing pulses are applied and modified responsive to signals indicative of cardiac function, as described above.

PCT patent application PCT/IL97/00236, which is assigned to the assignee of the present patent application and is incorporated herein by reference, also describes a pacemaker that gives cardiac output enhancement. This pacemaker applies both excitatory (pacing) and non-excitatory electrical stimulation pulses to the heart. By applying non-excitatory pulses of suitable strength, appropriately timed with respect to the heart's electrical activation, the contraction of selected segments of the heart muscle can be increased or decreased, thus increasing or decreasing the stroke volume of the heart.

Concepts of cardiac muscle stimulation are also described in the above-mentioned PCT patent application PCT/IL97/00012. This application describes the use of non-excitatory electric fields, applied via electrodes to selected areas of the heart muscle, to modify the muscular function and, inter alia, to strengthen a portion of the muscle and engender redistribution of cardiac muscle mass. Similarly, in a preferred embodiment of the present invention, extended pacing signals are applied to one or more selected areas of the heart in such a manner as to engender muscle mass redistribution. Such redistribution can have the effect not only of locally strengthening the heart muscle, but also improving the muscular performance and efficiency of the entire heart.

Although preferred embodiments are described herein with reference to pacing of the heart, it will be appreciated that the principles of the present invention may similarly be applied to pacing of other muscles, particularly smooth muscles, such as the larynx, esophagus, uterus, intestines or bladder, or of other excitable tissue, such as hormonal glands.

There is therefore provided, in accordance with a preferred embodiment of the present invention, apparatus for heart pacing with hemodynamic improvement, including:

one or more electrodes, which convey electrical signals to respective cardiac muscle segments; and signal generation circuitry, which applies an extended pacing signal, having an overall duration greater than three times a chronaxie time, to the one or more electrodes so as to pace the heart.

There is also provided, in accordance with a preferred embodiment of the present invention, a method for heart pacing with enhancement of cardiac contraction, including:

applying one or more electrodes to a subject's heart; and conveying an extended pacing signal, having an overall duration of at three times a chronaxie time, to the one or more electrodes so as to pace the heart.

Preferably, the overall duration is at least 10 ms, and more preferably at least 20 ms, but less than approximately 100 ms.

Preferably, the cardiac muscle segments to which the one or more electrodes are applied are characterized by a refractory period, and the overall duration of the signal is such that the signal terminates during the refractory period.

In a preferred embodiment, the signal has a leading edge and a trailing edge, and wherein the trailing edge is characterized by an absolute rate of voltage change substantially smaller than that of the leading edge. Preferably, the absolute rate of the voltage change is less than a minimum rate of change necessary to generate an action potential in the cardiac muscle segments.

Preferably, the signal has an amplitude at least three times as great as a threshold for pacing the heart, but not sufficient for cardioversion and, further preferably, a duration at least three times a threshold duration for pacing the heart at the amplitude of the signal.

There is further provided, in accordance with a preferred embodiment of the present invention, apparatus for heart pacing with hemodynamic improvement, including:

one or more electrodes, which convey electrical signals to respective cardiac muscle segments; and signal generation circuitry, which applies an extended pacing signal, including a train of a plurality of biphasic pulses, to the one or more electrodes so as to pace the heart.

There is additionally provided, in accordance with a preferred embodiment of the present invention, a method for heart pacing with hemodynamic enhancement, including:

applying one or more electrodes to the heart; and conveying an extended pacing signal, including a train of a plurality of biphasic pulses, to the one or more electrodes so as to pace the heart.

Preferably, each of the pulses in the train preferably has a pulse duration of at least 1 ms, and wherein the pulse train has a period of at least 5 ms, and more preferably of at least 20 ms. Preferably, the train of pulses includes a plurality of biphasic pulses. Further preferably, the train of pulses has a duty cycle between about 10% and 50%.

Preferably, the train of pulses includes square wave pulses or, alternatively, sinusoidal pulses.

There is moreover provided, in accordance with a preferred embodiment of the present invention, apparatus for heart pacing with hemodynamic enhancement, including:

one or more electrodes, which convey electrical signals to respective cardiac muscle segments; and signal generation circuitry, which applies an extended pacing signal to the one or more electrodes so as to pace the heart, the signal having an amplitude at least three times as great as a threshold for pacing the heart, but not sufficient for cardioversion.

There is also provided, in accordance with a preferred embodiment of the present invention, a method for heart pacing with hemodynamic enhancement, including:

applying one or more electrodes to the heart; and conveying an extended pacing signal to the one or more electrodes so as to pace the heart, the signal having an amplitude at least three times as great as a threshold for pacing the heart, but not sufficient for cardioversion.

Preferably, the signal has a duration at least three times a threshold duration for pacing the heart at the amplitude of the signal.

Preferably, application of the extended pacing signal modifies a characteristic of pulsatile flow of blood in the heart.

In a preferred embodiment, application of the extended pacing signal increases a stroke volume of the heart by at least 5%, and preferably by at least 10%, relative to the stroke volume when the heart is paced with pulses less than 2 ms in duration.

In another preferred embodiment, application of the extended pacing signal modifies a cardiac output of the heart by at least 5% relative to the cardiac output when the heart is paced with pulses less than 2 ms in duration at a pacing rate equal to that of the extended pacing signal.

In yet another preferred embodiment, application of the extended pacing signal increases a contractility of at least a portion of the heart by at least 10% relative to the contractility thereof when the heart is paced with pulses less than 2 ms in duration. Alternatively, application of the extended pacing signal decreases a contractility of at least a portion of the heart by at least 10% relative to the contractility thereof when the heart is paced with pulses less than 2 ms in duration.

In a preferred embodiment, application of the extended pacing signal modifies a muscular tension in the heart by at least 10% relative to the tension when the heart is paced with pulses less than 2 ms in duration.

Preferably, application of the extended pacing signal modifies the duration of an action potential in the respective cardiac muscle segments by at least 10% relative to the duration when the heart is paced with pulses less than 2 ms in duration.

Preferably, the signal generation circuitry includes a pulse generator and a DC offset generator, whose outputs are summed to provide the extended pacing signal.

In a preferred embodiment, the one or more electrodes include a plurality of electrodes, which are positioned in different chambers of the heart. Preferably, the signal includes a plurality of waveforms, which are applied respectively to the electrodes in the different chambers according to a predetermined time sequence. Further preferably, a pacing pulse having a duration less than 8 ms is applied to one or more of the electrodes positioned in a first one of the different chambers, and the extended pacing signal is applied to another one or more of the electrodes positioned in a second one of the different chambers.

In a preferred embodiment, the signal generation circuitry applies the extended pacing signal to the one or more electrodes in response to a demand for an enhancement of hemodynamic performance of the heart, wherein the enhancement of hemodynamic performance preferably includes an increase in cardiac output. Preferably, the apparatus includes a sensor which generates an output responsive to a physiological parameter indicative of the demand for the enhancement, wherein the signal generation circuitry applies the extended pacing signal responsive to the output from the sensor. Alternatively or additionally, in the absence of the demand for the enhancement, the signal generation circuitry applies pacing pulses to the electrodes of substantially lower energy than the extended pacing signal.

Preferably, the one or more electrodes include endocardial electrodes. Alternatively or additionally, the one or more electrodes include epicardial electrodes, transmyocardial electrodes or transvenous electrodes.

In a preferred embodiment, the apparatus includes a sensor, preferably an electrode, coupled to generate a signal responsive to activity of the heart, wherein the signal generation circuitry receives the signal from the sensor and modifies the extended pacing signal responsive thereto.

In a preferred embodiment, the electrode senses a Monophasic Action Potential signal.

In another preferred embodiment, the sensor includes a pair of closely-spaced bipolar electrodes, which sense a local endocardial action potential.

Preferably, the signal generation circuitry detects a possible arrhythmic stimulation of the heart and modifies the extended pacing signal so as to prevent the arrhythmic stimulation.

In a preferred embodiment, the one or more electrodes are applied such that conveying the extended pacing signal engenders a redistribution of cardiac muscle mass.

The present invention will be more fully understood from the following detailed description of the preferred embodiments thereof, taken together with the drawings in which:

DETAILED DESCRIPTION OF PREFERRED EMBODIMENTS

Figure 2:
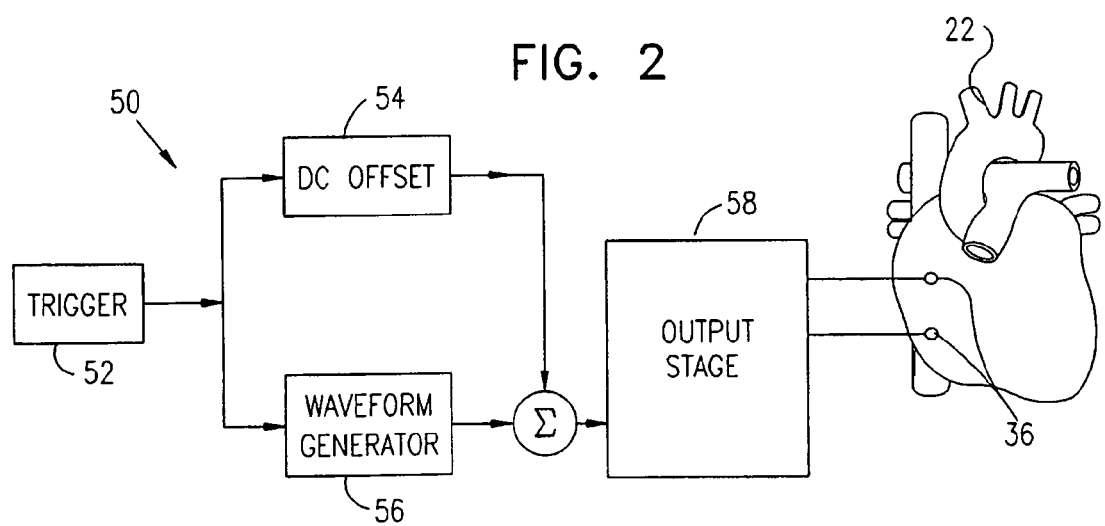
FIG. 2 is a schematic block diagram illustrating a pulse train generator for applying extended pacing signals to a heart, in accordance with a preferred embodiment of the present invention.

Reference is now made to FIG. 2, which is a schematic block diagram illustrating a pulse train generator 50, which generates and applies extended pacing signals to heart 22 via electrodes 36, in accordance with a preferred embodiment of the present invention. Generator 50 is preferably used as part of a complete pacing system (shown below in FIG. 6), but it has also been used by the inventors in experimental assessment of the principles of the present invention, as described hereinbelow with reference to FIGS. 4 and 5.

Generator 50 comprises a waveform generator 56 and, preferably, a DC offset generator 54, which are synchronized by a trigger generator 52. The outputs of the waveform and DC offset generators are summed and input to an output stage 58, which preferably comprises a voltage output stage or, alternatively, a voltage-to-current converter. Trigger generator 52, waveform generator 56, DC offset generator 54 and output stage 58 comprise electrical elements that are known in the pacemaking art, but are suitably modified to provide relatively longer pulses and higher energy levels.

Figure 3A:
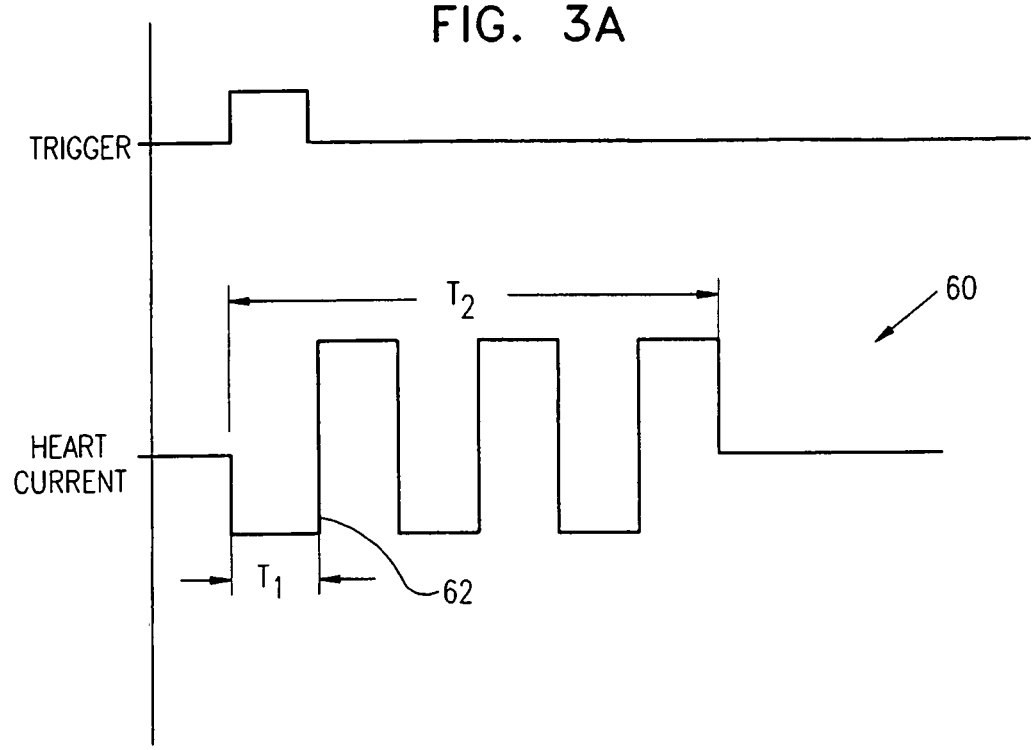
FIG. 3A is a schematic timing diagram illustrating a signal applied by the generator of FIG. 2, in accordance with a preferred embodiment of the present invention.

FIG. 3A is a timing diagram illustrating an extended signal 60 applied by generator 50 to electrodes 36, in accordance with a preferred embodiment of the present invention. The signal preferably comprises a train of biphasic pulses, having an overall duration $T_2$, which is preferably at least three times the chronaxie time, and is most preferably at least 10 ms and no more than about 100 ms. Preferably, the signal begins with an initial cathodic pulse 62, and has a period $T_1$ which is most preferably approximately 20 ms, but may be either longer or shorter. The signal peak-to-peak amplitude is preferably at least three times the threshold, unlike pacemakers known in the art, which generally operate at no more than twice the pacing threshold. Although signal 60 is shown as having a duty cycle of approximately 50%, a lower duty cycle is also possible, preferably as low as 10% in order to reduce energy expenditure. When a low duty cycle is used, initial pulse 62 may itself have a duration as short as 1 ms, or even less. Various other possible extended pacing signals, in accordance with preferred embodiments of the present invention, are shown and described hereinbelow.

Signal 60 is shown in FIG. 3A as comprising a periodic train of three biphasic (cathodic plus anodic) square wave pulses, as signals comprising two or more biphasic pulses have been found to give the greatest relative increase in cardiac output, by comparison with ordinary pacing pulses known in the art. The pulse train preferably has a repetition frequency between 50 and 200 Hz (period between 5 and 20 ms), for maximal enhancement of hemodynamic function, and is superimposed on a DC offset. Other signals may also be used, however, for example:

- a single extended pulse, either cathodic or anodic;
- one or more biphasic pulses that begin with an anodic pulse, rather than with the cathodic pulse as shown in the figure;
- a train of uniphasic pulses, either cathodic or anodic;
- a train of pulses having non-square shape, such as sinusoidal pulses; or
- a pulse train including more or fewer pulses than are shown in the figure.

Furthermore, pulses in the train may have a substantially uniform amplitude, or the pulse amplitudes may vary according to a predetermined envelope function.

An essential feature of signal 60 is its long overall duration $T_2$, which must be substantially greater than the duration of pacing pulses commonly used in the art. Preferably, the period of the signal, $T_1$, is itself also substantially longer than ordinary pacing pulses. As noted hereinabove, in order to generate action potentials in the heart, pacing pulses need have a duration of no more than 1-2 ms, whereas $T_1$ is several times that long, and $T_2$ is many times longer. Therefore, only a small, initial fraction of signal 60 is needed for actually pacing the heart, and the remainder of the energy in the signal is applied to increase the contractility. $T_2$ is preferably kept less than about 100 ms in order to reduce or eliminate the likelihood that a later portion of signal 60 will give rise to an additional, arrhythmic stimulation of the heart tissue.

Figure 3B:
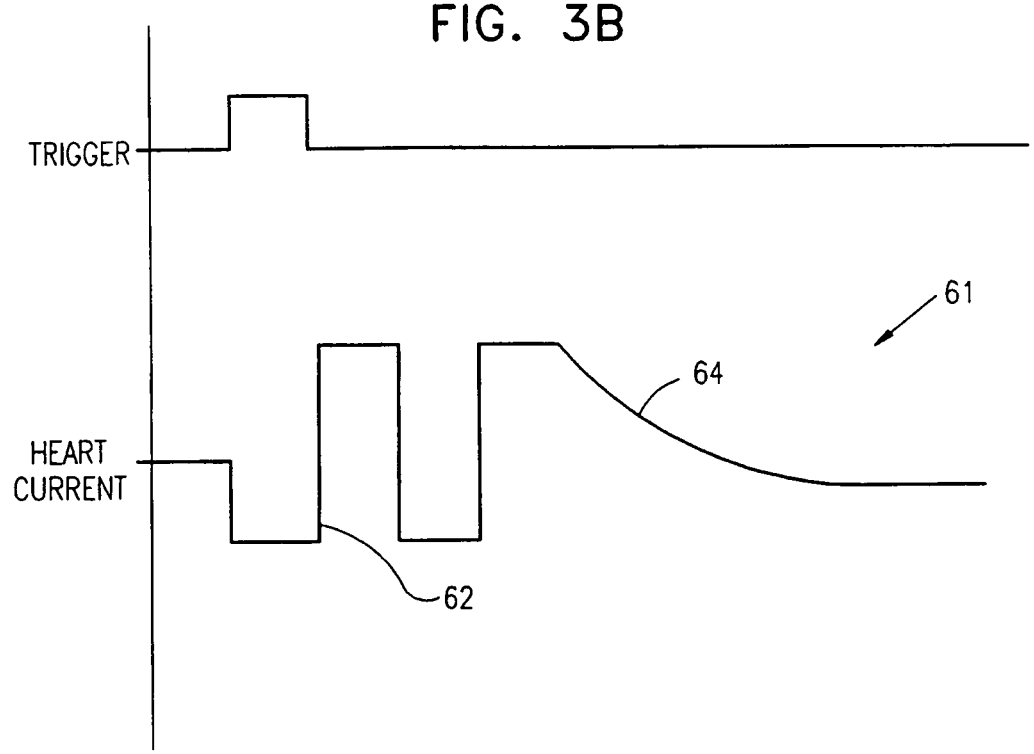
FIG. 3B is a schematic timing diagram illustrating a signal applied by the generator of FIG. 2, in accordance with an alternative preferred embodiment of the present invention.

FIG. 3B is a timing diagram showing a signal 61 in accordance with an alternative preferred embodiment of the present invention. Signal 61 is substantially similar to signal 60, shown in FIG. 3A and described hereinabove, except that it has a relatively long, smoothly-decaying trailing edge 64. Preferably, the decay of edge 64 is generally exponential. Because of the slow decay of edge 64, the magnitude of the rate of change of the voltage (dV/dt) applied to heart 22 by electrodes 36 in this portion of the signal will be relatively small, by comparison with the sharp trailing edge of signal 60. Therefore, the likelihood of an undesired, arrhythmic stimulation due dV/dt of the trailing edge is substantially reduced when signal 61 is used.

Figure 4:
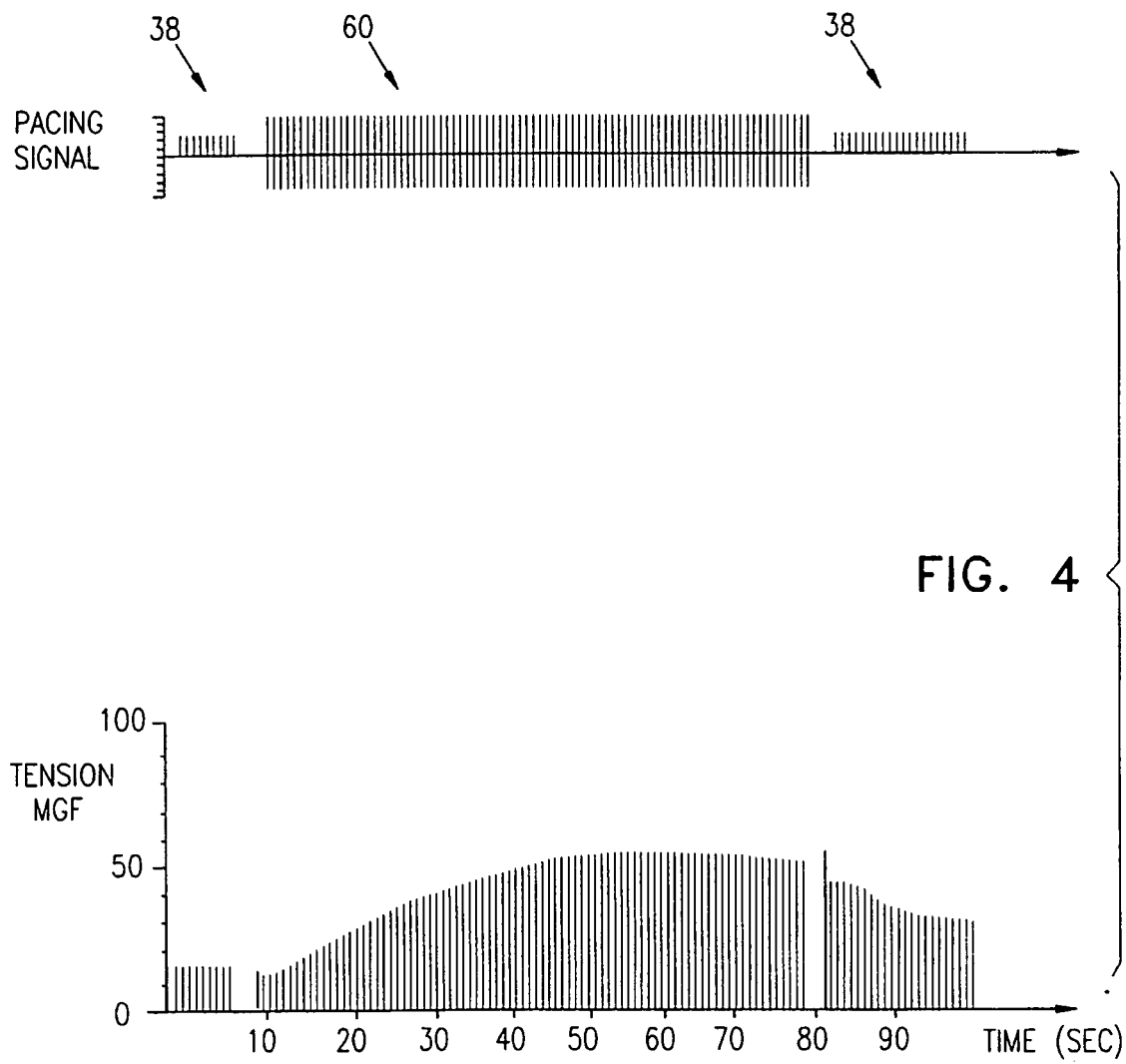
FIG. 4 is a graph that schematically illustrates experimental results showing increased muscular tension obtained upon application of extended pacing signals to muscle fibers, in accordance with a preferred embodiment of the present invention.

FIG. 4 is a graph showing experimental measurements of muscular tension as a result of pacing with extended pacing signals, in accordance with a preferred embodiment of the present invention. Carbon electrodes were fixed to a rabbit right papillary muscle, which was paced at 1 Hz. A muscle tendon was hooked onto a force transducer (D-7806 DC Bridge Amplifier, with ±10 gram input range, produced by Hugo Sachs Electronics, Germany). The muscle was hooked at an optimal muscle length for enabling isometric contraction measurements. The tension was monitored and recorded at a rate of 1000 Hz per channel, with A/D resolution of 12 bits.

Figure 1A:
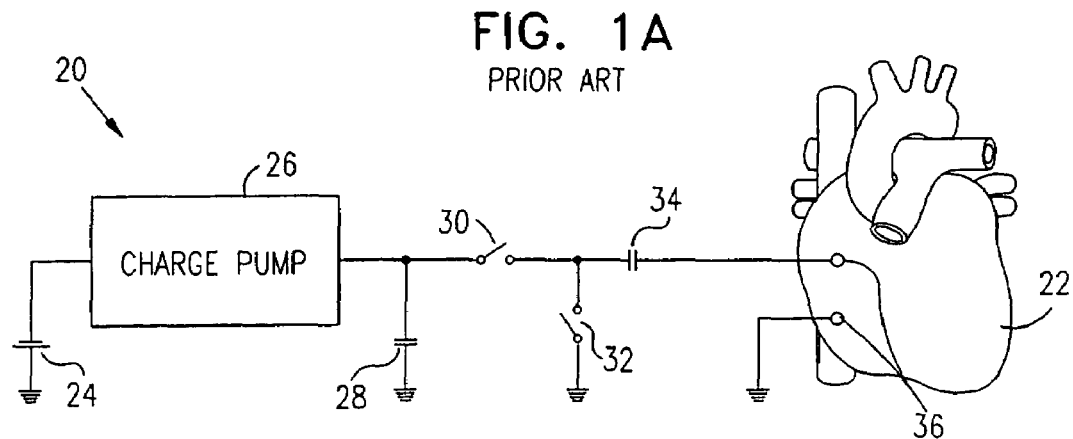
FIG. 1A is a schematic electrical diagram of a pacemaker pulse generator, as is known in the art.
Figure 1B:
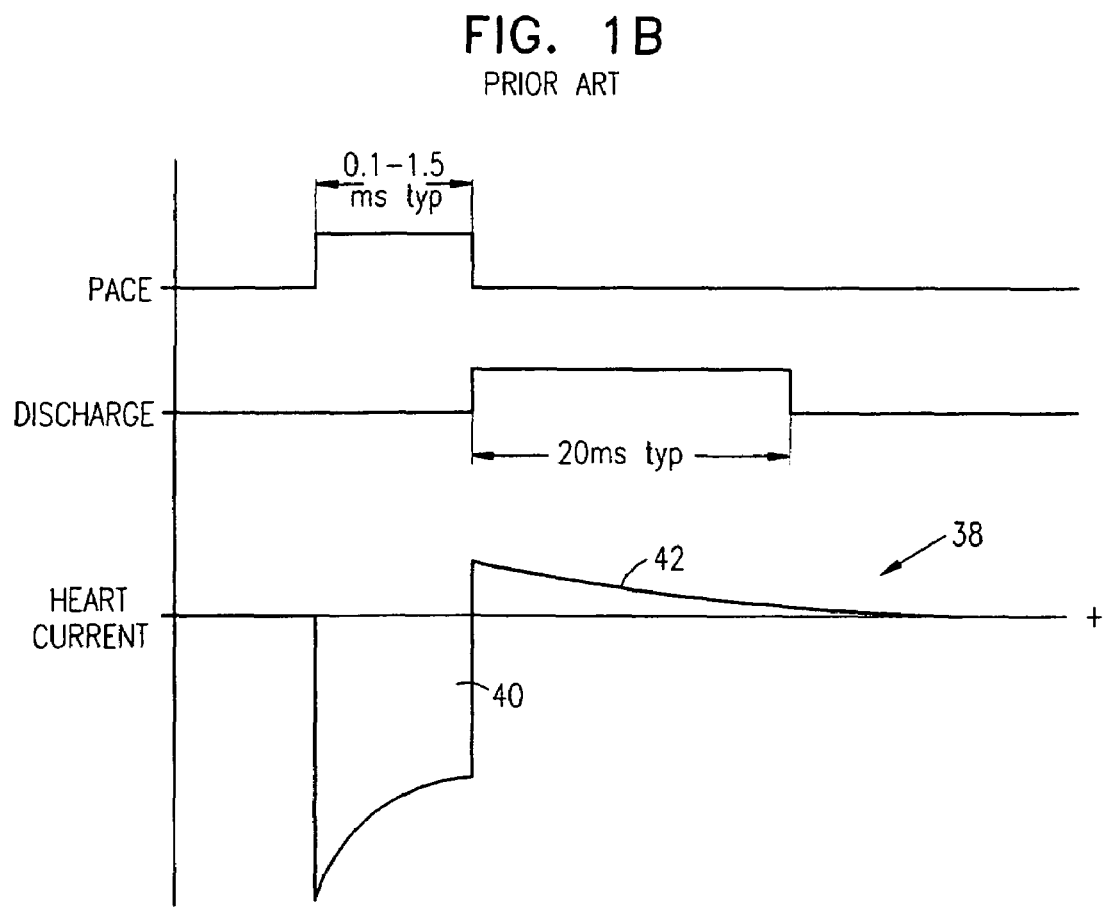
FIG. 1B is a timing diagram illustrating signals associated with the pacemaker of FIG. 1.

Initially, the muscle was paced with a conventional pacing signal, such as waveform 38 (FIG. 1B). An extended signal similar to signal 60, was then applied, having a period $T_1=10$ ms and duration $T_2=60$ ms and a peak-to-peak amplitude of 6 mA. The tension of the muscle was observed to increase gradually over a period of 30-40 sec, until it leveled off at about 3-4 times its initial value, which was measured under conventional pacing. When the extended signal was discontinued, and conventional pacing resumed, the tension dropped gradually back to its previous value.

Figure 5:
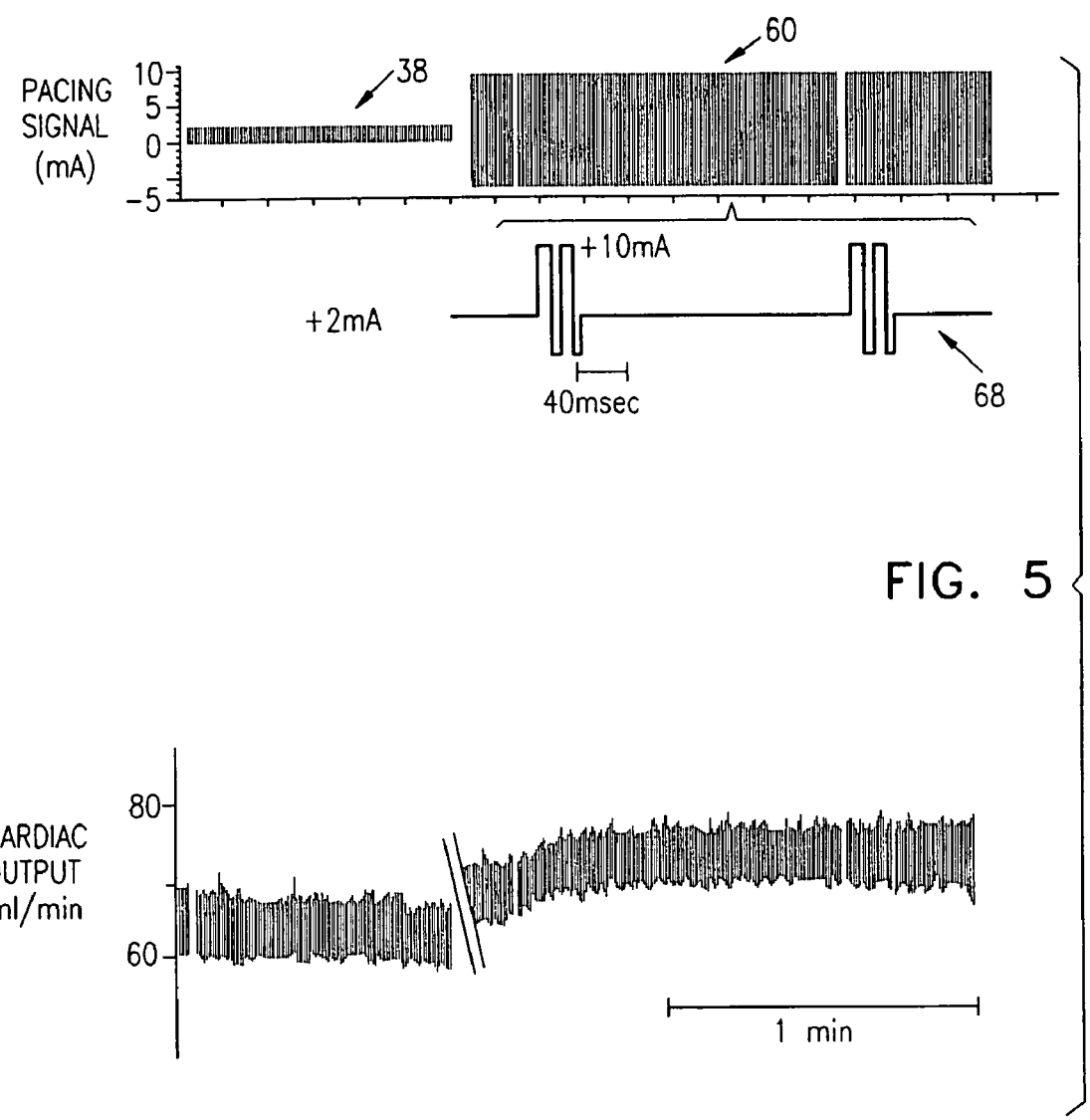
FIG. 5 is a graph that schematically illustrates experimental results showing an enhancement of cardiac output due to application of extended pacing signals, in accordance with a preferred embodiment of the present invention.

FIG. 5 is a graph showing further experimental results, illustrating an increase in cardiac output due to pacing with extended pacing pulses, in accordance with a preferred embodiment of the present invention. A rabbit heart was dissected out and perfused with a balanced isotonic solution, using the Langerdorff working heart apparatus, under standard experimental conditions known in the art. Two graphite vacuum electrodes were epicardially positioned at the left ventricle of the heart, and the pacing signal shown at the top of FIG. 5 was applied between the electrodes. Initially, with a conventional pacing signal such as waveform 38, mean cardiac output was measured to be 65 ml/min. An extended signal similar to signal 60 was then applied, and the cardiac output was observed to rise gradually to about 75 ml/min, which was maintained for as long as the extended signal was applied, a period of 2 min. In this case, as shown by an inset 68 in FIG. 5, the extended signal comprises two biphasic pulses, each beginning with an anodic pulse having an amplitude of about 10 mA, followed by a cathodic pulse of about 6 mA, with a DC level of about +2 mA. The overall signal duration $T_2$ was about 40 ms. Since the heart rate was held constant, at 180 beats/min, the increase in cardiac output was attributable to an increase in the heart's stroke volume.

Figure 6A:
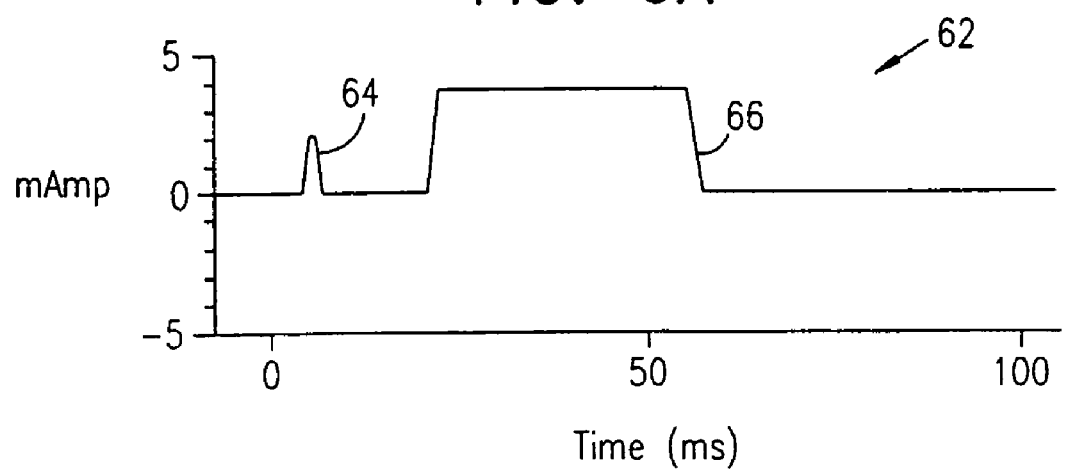
FIG. 6A is a graph that schematically illustrates an extended pacing signal, in accordance with another preferred embodiment of the present invention.

FIG. 6A schematically illustrates another extended pacing signal 62, in accordance with a preferred embodiment of the present invention. Signal 62 comprises a train of two anodic pulses: an initial, relatively short pulse 64, approximately 2 ms long and has an amplitude of 2 mA, followed by a longer pulse 66 having a duration of 30-40 ms and variable amplitude.

Figure 6B:
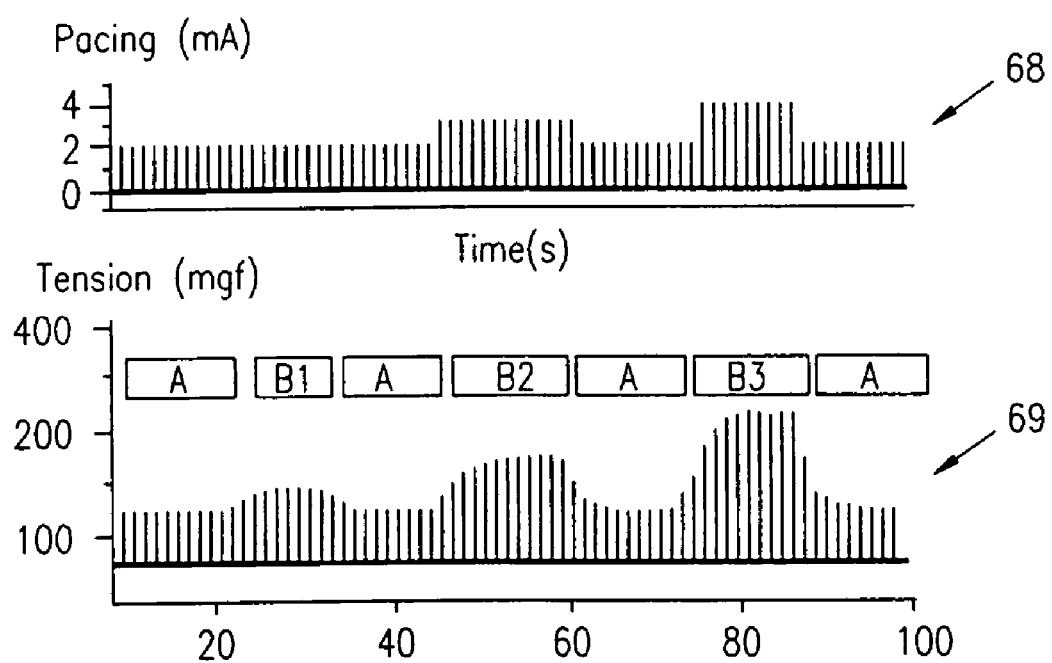
FIG. 6B is a graph that schematically illustrates experimental results obtained using pacing signals of the form shown in FIG. 6A.

FIG. 6B shows experimental measurements of changes in muscle tension due to application of signal 62, in which the amplitude of pulse 66 was varied, in accordance with a preferred embodiment of the present invention. In this figure, an upper trace 68 shows the applied pacing signal, and a lower trace 69 shows the muscle tension measurement. A rabbit right papillary muscle was placed in an organ bath and perfused continuously with Krebs solution at 37° C. The muscle was stretched to an optimal length (Lmax), and its isometric tension was sampled at 1000 Hz. The muscle was paced unipolarly by applying signal 62 through a Teflon-coated platinum-iridium wire (0.125 mm diameter) at 1 Hz, against two reference electrodes (uncoated graphite, 0.9 mm diameter) at either end of the bath.

Pacing of the muscle was divided into several periods, labeled in FIG. 6B, during which the amplitude of pulse 66 was set to different values, as given by Table I, below:

TABLE I

| Period | Amplitude of pulse 66 |
| --- | --- |
| A (control) | Zero |
| B1 | 2 mA |
| B2 | 3 mA |
| B3 | 4 mA |

As can be seen in FIG. 6B, the muscle tension increased strongly, nearly doubling from its control level (A) to that obtained during period B3.

Figure 7:
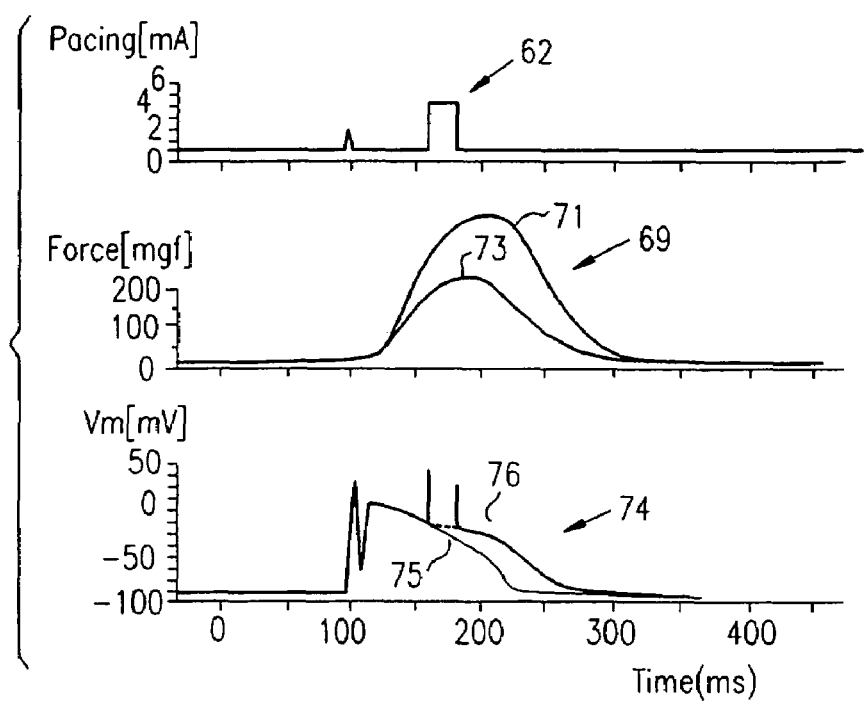
FIG. 7 is a graph schematically illustrating modulation of contraction force and action potentials using the pacing signal of FIG. 6A.

FIG. 7 schematically illustrates further experimental results obtained using pacing signal 62, in accordance with a preferred embodiment of the present invention. Trace 69 in FIG. 7 illustrates a detail of the force measurements shown in FIG. 6B, wherein a pressure wave 71 obtained during period B3 is seen to be substantially higher and longer than a corresponding wave 73 measured under conventional pacing during the control period.

Trace 74 in FIG. 7 shows measurements of action potentials obtained under the conditions described with reference to FIG. 6B. An ordinary potential 75 obtained during the control period has a duration of about 100 ms. During period B3, however, a lengthened action potential 76 is obtained, having a duration of about 150 ms. (An initial portion of potential 76 overlaps in shape and amplitude with potential 75 and is therefore indistinguishable from it in the figure.) Similar lengthening of the action potentials, relative to those measured under conventional pacing, has also been observed to occur when other types of extended pacing signals are applied, in accordance with the principles of the present invention.

By comparison, in the article by Thakor et al., mentioned above, action potentials were observed to propagate faster through the tissue, but no extension of their duration was reported. Furthermore, although Thakor observed slightly increased pressure and faster pressure onset in isolated muscle fibers, he did not measure or report an increase in cardiac output, as the present invention has been shown to engender. The range of signal durations (2-8 ms) and the total energy applied to the heart in Thakor's experiments were both roughly an order of magnitude less than corresponding values in preferred embof the present invention, as described hereinabove. The enhancement of cardiac output observed by the present inventors due to the use of extended pacing signals, and the pacing methods and pacemaker apparatus based thereon, are therefore believed to be substantively different from those reported by Thakor or by other investigators and to represent a more advantageous form of therapy.

Figure 8:
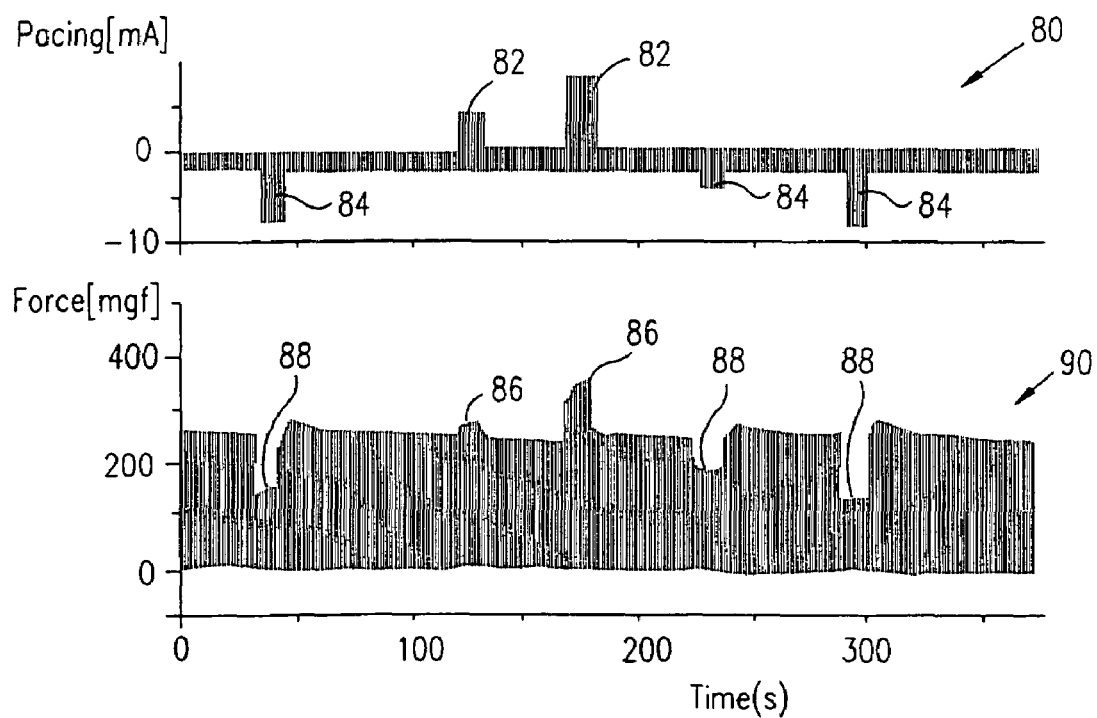
FIG. 8 is a graph schematically showing further experimental results, in accordance with a preferred embodiment of the present invention.

FIG. 8 is a graph that schematically illustrates further experimental results, in accordance with a preferred embodiment of the present invention, in which extended pacing signals are used alternatively to increase and to decrease muscular force. Decreasing the muscular force may be useful under some clinical conditions in order to reduce local strain on the heart muscle and to engender a redistribution of the heart's work load among different areas of the heart.

An upper trace 80 in FIG. 8 shows unipolar pacing signals applied to the heart, wherein positive peaks 82 indicate application of anodic extended pacing signals, and negative peaks 84 indicate cathodic extended pacing signals. The extended pacing signals have the general form of signal 62, shown in FIG. 6A except that the cathodic signals are inverted. The remainder of trace 80, other than the peaks, represents conventional pacing.

A lower trace 90 in the figure shows measurements of tension made under the general conditions described above with reference to FIG. 6B. The anodic extended pacing signals engendered increased contractile force of the muscle, whereas the cathodic extended pacing signals had the opposite effect. The magnitude of the increase or decrease was generally proportional to the amplitude of pulse 66.

Figure 9:
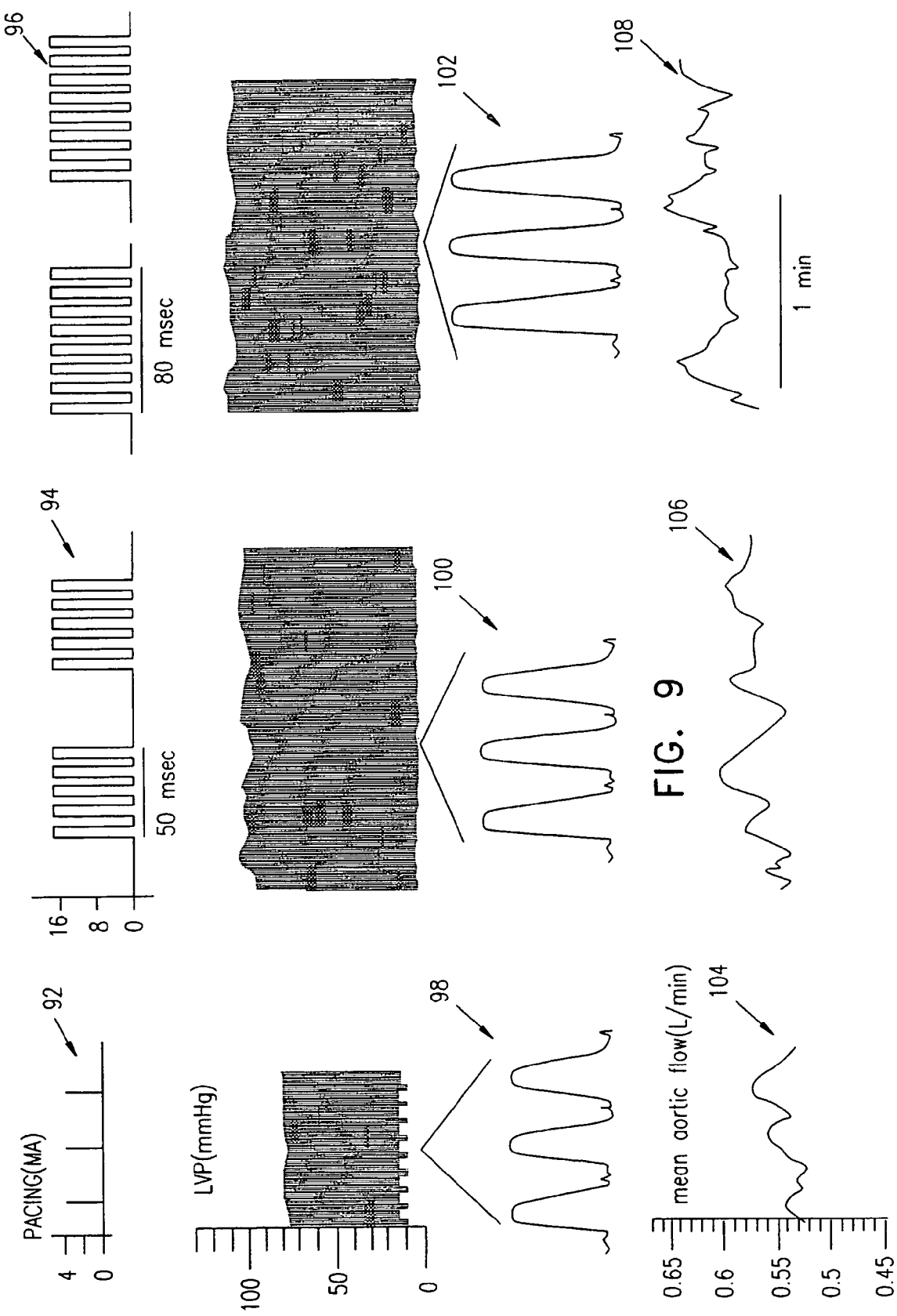
FIG. 9 is a graph that schematically shows enhancement of ventricular pressure and aortic flow due to application of extended pacing signals, in accordance with another preferred embodiment of the present invention.

FIG. 9 schematically illustrates further experimental results, showing the influence of extended pacing signals 94 and 96 in enhancing the heart's pulsatile flow, in accordance with a preferred embodiment of the present invention. In these experiments, a 27 kg dog was anesthetized with chloralose-urethane, intubated to the trachea and mechanically ventilated. After chest surgery, the dog's pericardium was opened, and carbon electrodes were placed epicardially at the right and left ventricles. A conventional pacing signal 92, of 4 mA amplitude and 2 ms duration, was applied (VOO mode) as a control at the right ventricle. Signal 92 was replaced for two-minute intervals with either signal 94 or 96, applied at the left ventricle. Signals 94 and 96 comprised anodic pulse trains having repetition frequencies of 100 Hz and amplitudes of 16 mA with respective overall durations of 50 and 80 ms.

In measurements of the dog's left ventricular pressure (LVP), it was observed that pacing with signal 96 caused the peak pressure to increase by 34-36% relative to the LVP under conventional pacing signal 92. Signal 94 caused a somewhat smaller pressure increase. The positive impact of the extended pacing signals on the heart's pulsatile flow is demonstrated by the increased amplitude of pressure waveforms 100 and 102, obtained when the extended pacing signals were used, relative to that of waveform 98 with conventional pacing. Furthermore, the mean aortic flow from the heart was observed to increase due to the extended pacing signals, up to about 12-13% more than the flow obtained under conventional pacing conditions.

Figure 10:
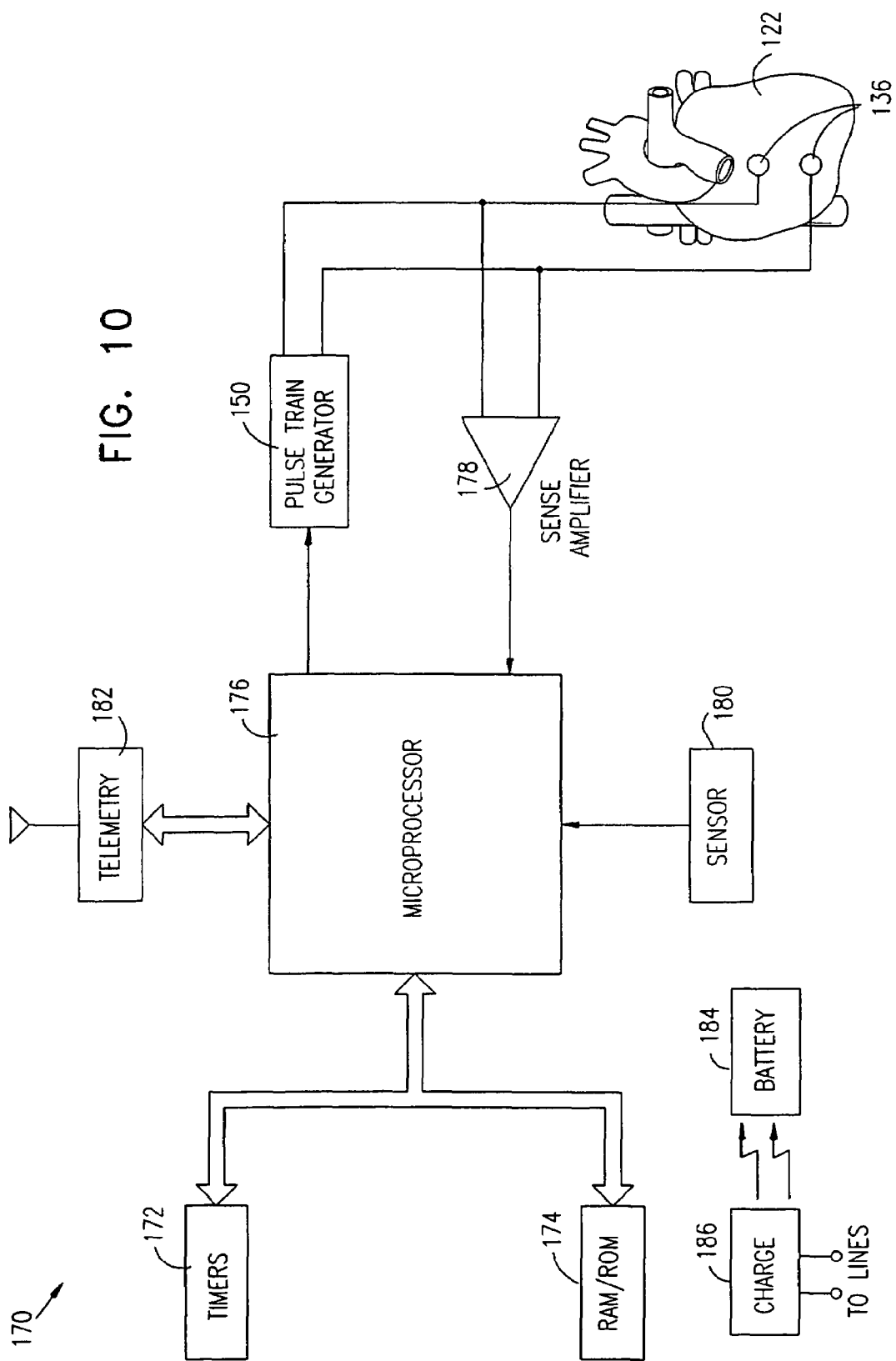
FIG. 10 is a schematic block diagram illustrating a pacemaker for applying extended pacing signals, in accordance with a preferred embodiment of the present invention.

FIG. 10 is a schematic block diagram showing a pacemaker 170 for application of extended pacing pulses via electrodes 36 to heart 22 of a patient, for the purpose of enhancing the contractility of the heart, in accordance with a preferred embodiment of the present invention. Pacemaker 170 is generally similar to implantable pacemakers known in the art, except that it is built around pulse train generator 50, as described hereinabove, and is programmed to apply extended pacing signals. Such signals may be applied substantially continuously, or they may be applied only as needed, for example, at certain hours of the day or upon demand by the patient, when the patient needs a boost in cardiac output.

Although electrodes 36 are shown only schematically in FIG. 10, it will be appreciated that a variety of different numbers and placements of the electrodes may be used. For example, pacemaker 170 may be coupled to drive more than two electrodes, which may be placed either in the same chamber or in multiple different chambers of the heart. The extended pacing signal, such as signal 60 (FIG. 3A) or signal 61 (FIG. 3B), may be applied to electrodes 36 in either unipolar or bipolar fashion. The electrodes are preferably placed endocardially, but may alternatively be placed epicardially, within a blood vessel, intramuscularly or in any other suitable location. The electrodes may be aligned along a normal conduction direction in the heart or perpendicular to the normal conduction direction. Preferably, the electrodes are placed in the heart responsive to a map of the heart's electrical and/or mechanical activity, in positions chosen so as to give a desired change in contraction of the heart muscle or, alternatively or additionally, to engender a desired redistribution of cardiac muscle mass. The electrodes preferably comprise highly conductive material with a large effective area, and are most preferably coated with a high-capacitance material, such as titanium nitride, iridium oxide, pyro-carbon or vitreous carbon.

In a preferred embodiment of the present invention, when more than two electrodes are used, the signals applied respectively to the electrodes are mutually timed so as to optimize the heart's systolic contraction. For example, one or more electrodes may be placed in one of the atria of the heart, and another one or more in the corresponding ventricle, in which case the signal is preferably applied first to the atrial electrodes. Alternatively, a conventional, low-energy pacing pulse may be applied to the atrial electrodes and an extended pacing signal applied after a delay to those in the ventricle. Similarly, electrodes may be applied in both right and left ventricles, with stimulation preferably applied first in the right ventricle. In any case, the signals are applied to the electrodes in such order and timing as to optimize hemodynamic performance.

Pacemaker 170 comprises a microprocessor 176, which is coupled to timer circuits 172 and memory 174 (RAM and/or ROM) and controls the operation of generator 50. The microprocessor and ancillary timer and memory circuits are substantially similar to such circuits and devices as are known in the pacemaking art. They differ from the prior art largely in that they are programmed to administer extended pacing signals, as described hereinabove, either instead of or in addition to conventional pacing signals. A sense amplifier 178, as is similarly known in the art, receives and amplifies electrogram signals from electrodes 36. These signals are conveyed to microprocessor 176, which preferably regulates the operation of generator 50 responsive to the signals.

A key purpose of sense amplifier 178 is to inhibit the delivery of the extended pacing signal at the time of the heart chamber's repolarization, so as to prevent undesired, arrhythmic stimulation of the heart. In a preferred embodiment of the present invention, one or more of electrodes 36 are used in Monophasic Action Potential (MAP) measurements of the heart's electrical activity, as are known in the art and described in the above-mentioned articles by Franz. To perform these measurements, a fixed potential is created, for example, by applying pressure at a location in the endocardium, and a unipolar action potential is measured by one or more of the electrodes relative to the fixed potential. Because the MAP measurements determine the action potential locally, the effect of "far-field" cardiac potentials is substantially reduced or eliminated. Such measurements can therefore be used to accurately monitorepolarization and sense local variations that may arise due to the extended pacing signal.

In another preferred embodiment, two of electrodes 36 are placed close together and used to capture electrophysiological signals using close bipolar sensing. A differential signal measured between the two electrodes reflects propagation of the action potentials in a small area, having dimensions on the order of the distance between the electrodes. The differential signal is thus used to determine the time of onset and the duration of the local action potential at the location of the electrode and to accurately observe changes in the action potential due to application of the extended pacing signals. As described above, microprocessor 176 preferably controls the extended pacing signal so that the pacing signal duration does not exceed that of the refractory period and discontinues the extended pacing signals if abnormal local electrical activity is observed to result from the pacing.

Thus, based on signals from amplifier 178, microprocessor 176 preferably detects a change in the local action potential indicative of a possible arrhythmic excitation of the heart due the signal, using the MAP measurement and/or other electrical parameters. When such a change is detected, the microprocessor limits the pacing signal duration accordingly, so as substantially not to exceed the length of the refractory period and avoid undesirable, arrhythmic stimulation. In addition, microprocessor 176 may be programmed so that pacemaker 170 functions as a rate-responsive pacemaker, introducing pacing pulses to electrodes 36 in response to detection of bradycardia, for example, or to other heart rate changes or arrhythmias, as is known in the art.

Preferably, a sensor 180 is coupled to heart 36 or elsewhere to the body of the patient, and provides an additional physiological input to microprocessor 176. Sensor 180 may comprise any suitable physiological sensor, or a plurality of sensors, known in the art. In particular, sensor 180 preferably comprises a stroke volume sensor or contractility sensor, such as a sensor based on intracardiac impedance measurement, as is known in the art, or alternatively or additionally, an oxygen sensor or pressure sensor. The sensor may then be used as part of a feedback loop, wherein microprocessor 176 controls the waveform generated by pulse train generator 50 in order to achieve and maintain a desired level of cardiac output.

Further preferably, microprocessor 176 is coupled by a wireless link, as is known in the art, to a telemetry system 182. This system is used in programming the microprocessor initially and in monitoring and adjusting its performance in later follow-up examinations of the patient.

As noted above, pacemaker 170 is preferably implanted in the patient's chest. It therefore preferably receives its power from a battery 184, which is suitably coupled to microprocessor 176, pulse train generator 50 and other power-consuming components. Because generator 50 applies substantially more energy to heart 22 than do pacemakers known in the art, the power drain on battery 184 is substantially higher. Therefore, battery 184 preferably comprises a rechargeable battery, for example, a lithium ion solid electrolyte type battery, as is known in the art. Periodically, battery 184 is recharged using a charger 186, which preferably charges the battery without forming a wired connection therewith, most preferably by inductive coupling of energy, as is generally known in the art.

It will be appreciated that the preferred embodiments described above are cited by way of example, and the full scope of the invention is limited only by the claims.

The invention claimed is:

1. Apparatus for heart pacing with hemodynamic improvement, comprising:
   one or more electrodes, which are adapted to convey electrical signals to respective cardiac muscle segments; and
   signal generation circuitry, which applies an extended pacing signal, having an overall duration greater than 8 ms, to the one or more electrodes so as to pace the heart,
   wherein the signal has a leading edge and a trailing edge, and wherein the trailing edge is characterized by an absolute rate of voltage change substantially smaller than that of the leading edge.

2. Apparatus according to claim 1, wherein the absolute rate of the voltage change is less than a minimum rate of change necessary to generate an action potential in the cardiac muscle segments.

3. A method for heart pacing with enhancement of cardiac contraction, comprising:
   applying one or more electrodes to a subject's heart; and
   conveying an extended pacing signal, having an overall duration greater than 8 ms, to the one or more electrodes so as to pace the heart,
   wherein the signal has a leading edge and a trailing edge, and wherein the trailing edge is characterized by an absolute rate of voltage change substantially smaller than that of the leading edge.

4. A method according to claim 3, wherein the absolute rate of the voltage change is less than a minimum rate of change necessary to generate an action potential in the cardiac muscle segments.

5. A method for heart pacing with enhancement of cardiac contraction, comprising:
   applying one or more implantable electrodes to a ventricle of a human subject's heart; and
   conveying an extended pacing signal to the one or more electrodes so as to pace the ventricle, the extended pacing signal having an overall duration greater than 8 ms from a time of initiation of application of that portion of the signal that initiates action potential propagation,
   wherein conveying the extended pacing signal comprises conveying a train of pulses,
   wherein the signal has an amplitude that is at least three times as great as a threshold for pacing the ventricle and that is sufficient neither for cardioversion nor for defibrillation, and
   wherein the cardiac muscle segments to which the one or more electrodes are applied are characterized by a refractory period, and wherein the overall duration of the signal is such that the signal terminates during the refractory period.

6. A method according to claim 5, wherein each of the pulses in the train has a pulse duration of at least 1 ms.

7. A method according to claim 6, wherein the train includes at least two pulses having a duration of at least 5 ms per pulse.

8. A method according to claim 5, wherein the train of pulses has a period of at least 5 ms.

9. A method according to claim 8, wherein the train of pulses has a period of at least 20 ms.

10. A method according to claim 5, wherein conveying the train of pulses comprises conveying a plurality of biphasic pulses.

11. A method according to claim 5, wherein the train of pulses has a duty cycle between about 10% and 50%.

12. A method according to claim 5, wherein conveying the extended pacing signal comprises modifying a characteristic of pulsatile flow of blood in the heart.

13. A method according to claim 12, wherein modifying the characteristic comprises increasing a stroke volume of the heart by at least 5% relative to the stroke volume when the heart is paced with pulses less than 2 ms in duration.

14. A method according to claim 13, wherein increasing the stroke volume comprises increasing the stroke volume by at least 10% relative to the stroke volume when the heart is paced with pulses less than 2 ms in duration.

15. A method according to claim 12, wherein modifying the characteristic comprises modifying a cardiac output of the heart by at least 5% relative to the cardiac output when the heart is paced with pulses less than 2 ms in duration at a pacing rate equal to that of the extended pacing signal.

16. A method according to claim 12, wherein modifying the characteristic comprises increasing a contractility of at least a portion of the heart by at least 10% relative to the contractility thereof when the heart is paced with pulses less than 2 ms in duration.

17. A method according to claim 12, wherein modifying the characteristic comprises decreasing a contractility of at least a portion of the heart by at least 10% relative to the contractility thereof when the heart is paced with pulses less than 2 ms in duration.

18. A method according to claim 12, wherein modifying the characteristic comprises modifying a muscular tension in the heart by at least 10% relative to the tension when the heart is paced with pulses less than 2 ms in duration.

19. A method according to claim 5, wherein conveying the extended pacing signal comprises modifying the duration of an action potential in the respective cardiac muscle segments by at least 10% relative to the duration when the heart is paced with pulses less than 2 ms in duration.

20. A method according to claim 5, wherein conveying the extended pacing signal increases a muscular tension in the respective cardiac muscle segments by at least 50% relative to the duration when the heart is paced with pulses less than 2 ms in duration.

21. A method according to claim 20, wherein conveying the extended pacing signal increases the muscular tension in the respective cardiac muscle segments by at least 100% relative to the duration when the heart is paced with pulses less than 2 ms in duration.

22. A method according to claim 5, wherein applying the one or more electrodes comprises applying a plurality of electrodes in different chambers of the heart.

23. A method according to claim 22, wherein conveying the extended pacing signal comprises conveying a plurality of waveforms respectively to the electrodes in the different chambers according to a predetermined time sequence.

24. A method according to claim 22, and comprising conveying a pacing pulse having a duration less than 8 ms to one or more of the electrodes positioned in a first one of the different chambers, and wherein conveying the extended pacing signal comprises conveying the signal to another one or more of the electrodes positioned in a second one of the different chambers.

25. A method according to claim 5, wherein conveying the extended pacing signal comprises conveying the signal to the one or more electrodes in response to a demand for an enhancement of hemodynamic performance of the heart.

26. A method according to claim 25, wherein the enhancement of hemodynamic performance comprises an increase in cardiac output.

27. A method according to claim 25, and comprising receiving an output signal responsive to a physiological parameter indicative of the demand for the enhancement, and wherein conveying the extended pacing signal comprises conveying the pacing signal responsive to the output signal.

28. A method according to claim 25, and comprising, in the absence of the demand for the enhancement, conveying pacing pulses to the electrodes of substantially lower energy than the extended pacing signal.

29. A method according to claim 5, wherein applying the one or more electrodes comprises applying electrodes endocardially.

30. A method according to claim 5, wherein applying the one or more electrodes comprises applying electrodes epicardially.

31. A method according to claim 5, wherein applying the one or more electrodes comprises applying electrodes transmyocardially.

32. A method according to claim 5, wherein applying the one or more electrodes comprises applying electrodes transvenously.

33. A method according to claim 5, and comprising receiving an output signal responsive to activity of the heart, and wherein conveying the extended pacing signal comprises modifying the pacing signal responsive to the output signal.

34. A method according to claim 33, wherein receiving the output signal comprises receiving an electrophysiological signal.

35. A method according to claim 34, wherein the electrophysiological signal comprises a Monophasic Action Potential signal.

36. A method according to claim 34, wherein receiving the electrophysiological signal comprises placing a pair of bipolar electrodes in close mutual proximity in contact with the ventricle and receiving a bipolar signal from the bipolar electrodes.

37. A method according to claim 32, wherein modifying the pacing signal comprises detecting a possible arrhythmic stimulation of the ventricle and modifying the extended pacing signal so as to prevent the arrhythmic stimulation.

38. A method according to claim 5, wherein applying the one or more electrodes comprises applying electrodes such that conveying the extended pacing signal engenders a redistribution of cardiac muscle mass.

39. A method according to claim 5, wherein the extended pacing signal comprises a plurality of extended pacing signals, wherein conveying comprises conveying the plurality of extended pacing signals so as to pace the heart by initiating a respective plurality of consecutive heartbeats, wherein each of the extended pacing signals has the overall duration greater than 8 ms from the time of initiation of application of that portion of the signal that initiates action potential propagation, wherein conveying each of the extended pacing signals comprises conveying the train of pulses, wherein each of the extended pacing signals has the amplitude that is at least three times as great as the threshold for pacing the heart and that is sufficient neither for cardioversion nor for defibrillation, and wherein the overall duration of each of the extended pacing signals is such that the signal terminates during the refractory period.

40. A method according to claim 5, wherein the overall duration of the extended pacing signal is greater than 10 ms.

41. A method according to claim 40, wherein the overall duration of the extended pacing signal is greater than 20 ms.

42. A method for heart pacing with enhancement of cardiac contraction, comprising:

applying one or more implantable electrodes to a human subject's heart; and conveying a plurality of extended pacing signals to the one or more electrodes so as to pace the heart by initiating a respective plurality of consecutive heartbeats, each of the extended pacing signals having an overall duration greater than 8 ms from a time of initiation of application of that portion of the signal that initiates action potential propagation, wherein conveying each of the extended pacing signals comprises conveying a train of pulses, wherein each of the extended pacing signals has an amplitude that is at least three times as great as a threshold for pacing the heart and that is sufficient neither for cardioversion nor for defibrillation, and wherein the cardiac muscle segments to which the one or more electrodes are applied are characterized by a refractory period, and wherein the overall duration of each of the extended pacing signals is such that the signal terminates during the refractory period.

43. A method according to claim 42, wherein applying the one or more electrodes comprises applying the one or more electrodes to a ventricle of the heart, wherein conveying comprises conveying the extended pacing signals to the one or more electrodes so as to pace the ventricle, and wherein the amplitude of each of the signals is at least three times as great as the threshold for pacing the ventricle.

44. A method according to claim 43, wherein the train includes at least two pulses having a duration of at least 5 ms per pulse.

45. A method according to claim 42, wherein each of the pulses in the train has a pulse duration of at least 1 ms.

46. A method according to claim 42, wherein the train of pulses has a period of at least 5 ms.

47. A method according to claim 46, wherein the train of pulses has a period of at least 20 ms.

48. A method according to claim 42, wherein conveying the train of pulses comprises conveying a plurality of biphasic pulses.

49. A method according to claim 42, wherein the train of pulses has a duty cycle between about 10% and 50%.

50. A method according to claim 42, wherein conveying the extended pacing signal comprises modifying a characteristic of pulsatile flow of blood in the heart.

51. A method according to claim 50, wherein modifying the characteristic comprises increasing a stroke volume of the heart by at least 5% relative to the stroke volume when the heart is paced with pulses less than 2 ms in duration.

52. A method according to claim 51, wherein increasing the stroke volume comprises increasing the stroke volume by at least 10% relative to the stroke volume when the heart is paced with pulses less than 2 ms in duration.

53. A method according to claim 50, wherein modifying the characteristic comprises modifying a cardiac output of the heart by at least 5% relative to the cardiac output when the heart is paced with pulses less than 2 ms in duration at a pacing rate equal to that of the extended pacing signal.

54. A method according to claim 50, wherein modifying the characteristic comprises increasing a contractility of at least a portion of the heart by at least 10% relative to the contractility thereof when the heart is paced with pulses less than 2 ms in duration.

55. A method according to claim 50, wherein modifying the characteristic comprises decreasing a contractility of at least a portion of the heart by at least 10% relative to the contractility thereof when the heart is paced with pulses less than 2 ms in duration.

56. A method according to claim 50, wherein modifying the characteristic comprises modifying a muscular tension in the heart by at least 10% relative to the tension when the heart is paced with pulses less than 2 ms in duration.

57. A method according to claim 42, wherein conveying the extended pacing signal comprises modifying the duration of an action potential in the respective cardiac muscle segments by at least 10% relative to the duration when the heart is paced with pulses less than 2 ms in duration.

58. A method according to claim 42, wherein conveying the extended pacing signal increases a muscular tension in the respective cardiac muscle segments by at least 50% relative to the duration when the heart is paced with pulses less than 2 ms in duration.

59. A method according to claim 58, wherein conveying the extended pacing signal increases the muscular tension in the respective cardiac muscle segments by at least 100% relative to the duration when the heart is paced with pulses less than 2 ms in duration.

60. A method according to claim 42, wherein applying the one or more electrodes comprises applying a plurality of electrodes in different chambers of the heart.

61. A method according to claim 60, wherein conveying the extended pacing signal comprises conveying a plurality of waveforms respectively to the electrodes in the different chambers according to a predetermined time sequence.

62. A method according to claim 60, and comprising conveying a pacing pulse having a duration less than 8 ms to one or more of the electrodes positioned in a first one of the different chambers, and wherein conveying the extended pacing signal comprises conveying the signal to another one or more of the electrodes positioned in a second one of the different chambers.

63. A method according to claim 42, wherein conveying the extended pacing signal comprises conveying the signal to the one or more electrodes in response to a demand for an enhancement of hemodynamic performance of the heart.

64. A method according to claim 63, wherein the enhancement of hemodynamic performance comprises an increase in cardiac output.

65. A method according to claim 63, and comprising receiving an output signal responsive to a physiological parameter indicative of the demand for the enhancement, and wherein conveying the extended pacing signal comprises conveying the pacing signal responsive to the output signal.

66. A method according to claim 63, and comprising, in the absence of the demand for the enhancement, conveying pacing pulses to the electrodes of substantially lower energy than the extended pacing signal.

67. A method according to claim 42, wherein applying the one or more electrodes comprises applying electrodes endocardially.

68. A method according to claim 42, wherein applying the one or more electrodes comprises applying electrodes epicardially.

69. A method according to claim 42, wherein applying the one or more electrodes comprises applying electrodes transmyocardially.

70. A method according to claim 42, wherein applying the one or more electrodes comprises applying electrodes transvenously.

71. A method according to claim 42, and comprising receiving an output signal responsive to activity of the heart, and wherein conveying the extended pacing signal comprises modifying the pacing signal responsive to the output signal.

72. A method according to claim 71, wherein receiving the output signal comprises receiving an electrophysiological signal.

73. A method according to claim 72, wherein the electrophysiological signal comprises a Monophasic Action Potential signal.

74. A method according to claim 72, wherein receiving the electrophysiological signal comprises placing a pair of bipolar electrodes in close mutual proximity in contact with the heart and receiving a bipolar signal from the bipolar electrodes.

75. A method according to claim 71, wherein modifying the pacing signal comprises detecting a possible arrhythmic stimulation of the heart and modifying the extended pacing signal so as to prevent the arrhythmic stimulation.

76. A method according to claim 42, wherein applying the one or more electrodes comprises applying electrodes such that conveying the extended pacing signal engenders a redistribution of cardiac muscle mass.

77. A method according to claim 42, wherein the overall duration of the extended pacing signal is greater than 10 ms.

78. A method according to claim 77, wherein the overall duration of the extended pacing signal is greater than 20 ms.

* * * * *